United States Patent [19]

Mathies et al.

[11] Patent Number: 6,028,190
[45] Date of Patent: Feb. 22, 2000

[54] PROBES LABELED WITH ENERGY TRANSFER COUPLED DYES

[75] Inventors: Richard Mathies, Moraga; Alexander Glazer, Orinda; Jingyue Ju, Redwood City, all of Calif.

[73] Assignee: The Regents of the University of California, Oakland, Calif.

[21] Appl. No.: 08/646,861

[22] Filed: May 8, 1996

Related U.S. Application Data

[63] Continuation-in-part of application No. 08/411,573, Mar. 27, 1995, abandoned, and a continuation-in-part of application No. 08/410,808, Mar. 27, 1995, Pat. No. 5,707,804, which is a continuation-in-part of application No. 08/189,924, Feb. 1, 1994, Pat. No. 5,654,419.

[51] Int. Cl.[7] .............................. C07H 21/02; C12Q 1/68
[52] U.S. Cl. ................................. 536/26.6; 435/6
[58] Field of Search .................. 536/24.3, 23.1, 536/23.2, 24.31, 24.32, 25.3, 26.6; 435/6, 91.1, 91.2; 204/182.8

[56] References Cited

U.S. PATENT DOCUMENTS

| | | | |
|---|---|---|---|
| 4,996,143 | 2/1991 | Heller et al. ................................ | 435/6 |
| 5,326,692 | 7/1994 | Brinkley et al. ........................... | 435/6 |
| 5,401,847 | 3/1995 | Glazer et al. . | |
| 5,538,848 | 7/1996 | Livak et al. ................................ | 435/5 |
| 5,573,909 | 11/1996 | Singer et al. .............................. | 435/6 |
| 5,591,578 | 1/1997 | Meade et al. .............................. | 435/6 |
| 5,614,386 | 3/1997 | Metzker et al. ........................ | 435/91.1 |

OTHER PUBLICATIONS

Stryer (1978) Ann. Rev. Biochem. 47:819–46.
Ozaki et al. (1992) Nucleic Acids Research 20:5205–14.
Ju et al. (1995) Proc. Natl. Acad. Sci. USA 92:4347–51.
Geoghegan et al. (1993) Bioconjugate Chemistry 4:537–44.
Murakami et al. (1994) Nucl. Acids Symp. Series No. 31, pp. 55–56.
Wang et al. (1996) Electrophoresis 17:1485–90.
Metzker et al. (Mar. 1996) Science 271:1420–22.
Hochstrasser (1994) Proc. SPIE—Int. Soc. Opt. Eng., 2137:775–81.
Maliwal et al. (1993) Biophysical Chemistry 46:273–81.
Parkhurst et al. (1995) Biochemistry 34:293–300.
Wu et al. (1996) J. Biol. Chem. 271:1470–74.
Bagwell et al. (1994) Nucleic Acids Research 22:2424–5.
Matsuoka et al. (1994) Tetrahedron: Asymmetry 5:2335–8.
Lee et al. (1994) Analytical Biochemistry 220:377–383.
Rye et al, Nucleic Acids Res 19: 327–333, 1990.

*Primary Examiner*—Eggerton A. Campbell
*Attorney, Agent, or Firm*—Townsend and Townsend and Crew LLP

[57] ABSTRACT

Fluorescent labels having at least one donor and at least one acceptor fluorophore bonded to a polymeric backbone in energy transfer relationship, as well as methods for their use, are provided. Of particular interest are the subject labels wherein the polymeric backbone is a nucleic acid and the donor fluorophore is bonded to the 5' terminus of said nucleic acid. Such labels find use as primers in applications involving nucleic acid chain extension, such as sequencing, PCR and the like.

27 Claims, 25 Drawing Sheets

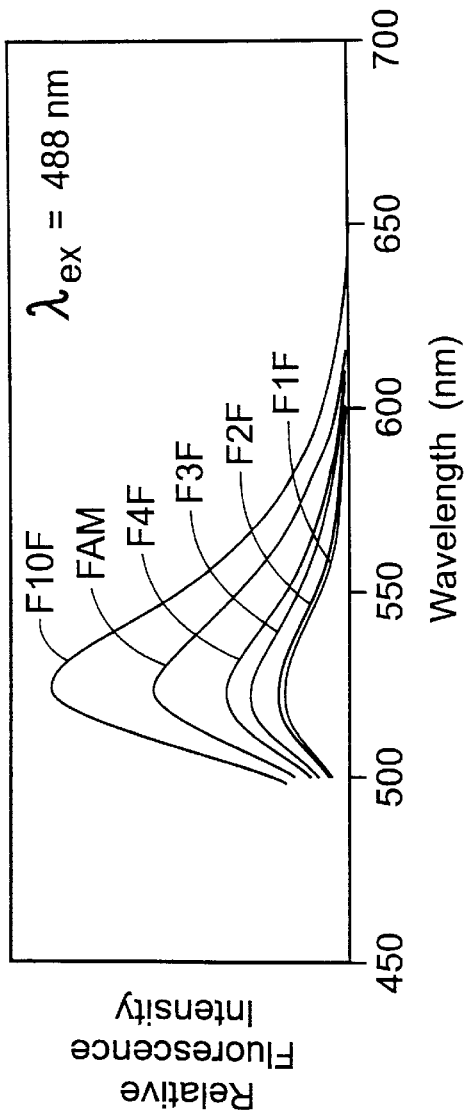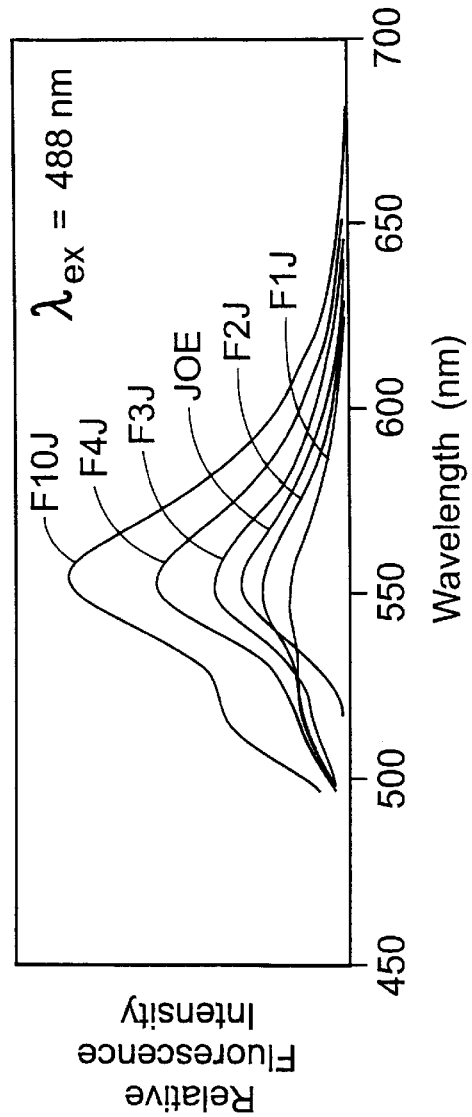
Fig. 10a
Fig. 10b

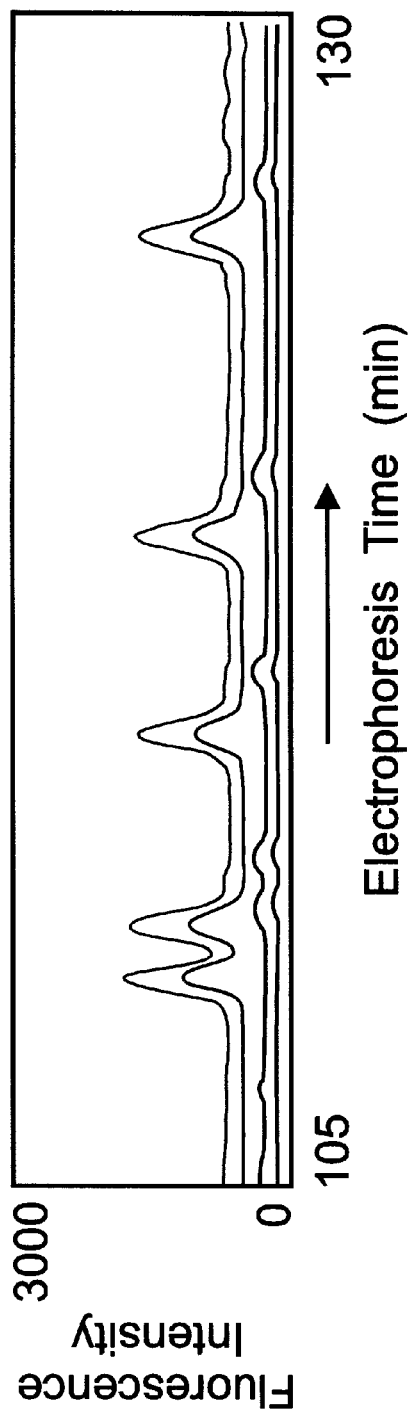
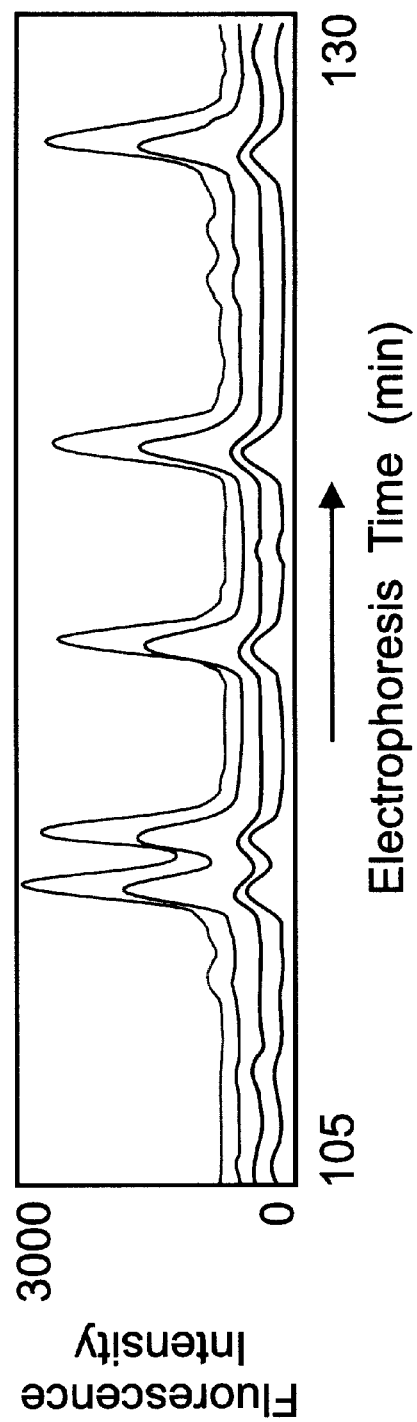
Fig. 14a
Fig. 14b

Scheme 1

F-1-(F,J,T,R)   FAM-5'-GT*TTTCCCAGTCACGACG-3'
                         |
                     (FAM, JOE, TAMRA, ROX)

F-2-(F,J,T,R)   FAM-5'-GTT*TTCCCAGTCACGACG-3'
                          |
                     (FAM, JOE, TAMRA, ROX)

F-3-(F,J,T,R)   FAM-5'-GTTT*TCCCAGTCACGACG-3'
                           |
                     (FAM, JOE, TAMRA, ROX)

F-4-(F,J,T,R)   FAM-5'-GTTTT*CCCAGTCACGACG-3'
                            |
                     (FAM, JOE, TAMRA, ROX)

F-10-(F,J,T,R)  FAM-5'-GTTTTCCCAGT*CACGACG-3'
                                 |
                     (FAM, JOE, TAMRA, ROX)

Fig. 23

Scheme 3

| | |
|---|---|
| VWFA-A (F8F) | FAM-5'-GAAAGCCCT*AGTGGATGATAAGAATAAT-3'<br>$\quad\quad\quad\quad\quad\quad\quad$ (CH$_2$)(CO)-NH-(CH$_2$)$_6$-NH-FAM |
| VWFA-B | 5'-GGACAGATGATAAATACATAGGATGGATGG-3' |
| THO1-A (F6F) | FAM-5'-GTGGGCT*GAAAAGCTCCCGATTAT-3'<br>$\quad\quad\quad\quad\quad\quad\quad$ (CH$_2$)(CO)-NH-(CH$_2$)$_6$-NH-FAM |
| THO1-B | 5'-ATTCAAAGGGTATCTGGGCTCTGG-3' |
| TPO-B (F8F) | FAM-5'-GGAGGAACT*GGGAACCACACAGGT-3'<br>$\quad\quad\quad\quad\quad\quad\quad$ (CH$_2$)(CO)-NH-(CH$_2$)$_6$-NH-FAM |
| TPO-A | 5'-ACTGGCACAGAACAGGCACTTAGG-3' |
| CSF-A (F8F) | FAM-5'-AACCTGAGT*CTGCCAAGGACTAGC-3'<br>$\quad\quad\quad\quad\quad\quad\quad$ (CH$_2$)(CO)-NH-(CH$_2$)$_6$-NH-FAM |
| CSF-B | 5'-TTCCACACACCACTGGCCATCTTC-3' |
| M13 (F10R) | FAM-5'-GTTTTCCCAGT*CACGACG-3'<br>$\quad\quad\quad\quad\quad\quad\quad$ (CH$_2$)(CO)-NH-(CH$_2$)$_6$-NH-ROX |

6,028,190

```
                          SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:1:

GTTTTCCCAG TC                                                         12

(2) INFORMATION FOR SEQ ID NO:2:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
```

(A) NAME/KEY: modified_base
            (B) LOCATION: 2
            (D) OTHER INFORMATION: /mod_base= OTHER
                /note= "N = thymidine modified by
                5-carboxyfluorescein through an
                aminohexylacrylimido linker"

(xi) SEQUENCE DESCRIPTION: SEQ ID NO:2:

NNTTTCCCAG TCACGACG                                                       18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 2
        (D) OTHER INFORMATION: /mod_base= OTHER
            /note= "N = thymidine modified by
            2',7'-dimethoxy-4',5'-dichloro-6-
            carboxyfluorescein through an
            aminohexylacrylimido linker"

(xi) SEQUENCE DESCRIPTION: SEQ ID NO:3:

NNTTTCCCAG TCACGACG                                                       18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 2
        (D) OTHER INFORMATION: /mod_base= OTHER
            /note= "N = thymidine modified by
            N,N,N',N'-tetramethyl-6-carboxyrhodamine
            through an aminohexylacrylimido linker"

(xi) SEQUENCE DESCRIPTION: SEQ ID NO:4:

NNTTTCCCAG TCACGACG                                                       18

(2) INFORMATION FOR SEQ ID NO:5:

(i) SEQUENCE CHARACTERISTICS:
        (A) LENGTH: 18 base pairs

```
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linker"

(ix) FEATURE:
            (A) NAME/KEY: modified_base
            (B) LOCATION: 2
            (D) OTHER INFORMATION: /mod_base= OTHER
                /note= "N = thymidine modified by
                6-carboxy-X-rhodamine through an
                aminohexylacrylimido linker"

(xi) SEQUENCE DESCRIPTION: SEQ ID NO:5:

NNTTTCCCAG TCACGACG                                                    18

(2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linkage"

(ix) FEATURE:
            (A) NAME/KEY: modified_base
            (B) LOCATION: 3
            (D) OTHER INFORMATION: /mod_base= OTHER
                /note= "N = thymidine modified by
                5-carboxyfluorescein through an
                aminohexylacrylimido linker"

(xi) SEQUENCE DESCRIPTION: SEQ ID NO:6:

NTNTTCCCAG TCACGACG                                                    18

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linker"

(ix) FEATURE:
            (A) NAME/KEY: modified_base
            (B) LOCATION: 3
```

```
            (D) OTHER INFORMATION: /mod_base= OTHER
                /note= "N = thymidine modified by
                2',7'-dimethoxy-4',5'-dichloro-6-
                carboxyfluorescein through an
                aminohexylacrylimido linker"

(xi) SEQUENCE DESCRIPTION: SEQ ID NO:7:

NTNTTCCCAG TCACGACG                                                    18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 3
        (D) OTHER INFORMATION: /mod_base= OTHER
            /note= "N = thymidine modified by
            N,N,N',N'-tetramethyl-6-carboxyrhodamine
            through an aminohexylacrylimido linker"

(xi) SEQUENCE DESCRIPTION: SEQ ID NO:8:

NTNTTCCCAG TCACGACG                                                    18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 3
        (D) OTHER INFORMATION: /mod_base= OTHER
            /note= "N = thymidine modified by
            6-carboxy-X-rhodamine through an
            aminohexylacrylimido linker"

(xi) SEQUENCE DESCRIPTION: SEQ ID NO:9:

NTNTTCCCAG TCACGACG                                                    18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
```

```
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:10:

NTTNTCCCAG TCACGACG                                                    18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by
            2',7'-dimethoxy-4',5'-dichloro-6-
            carboxyfluorescein through an
            aminohexylacrylimido linker"

(xi) SEQUENCE DESCRIPTION: SEQ ID NO:11:

NTTNTCCCAG TCACGACG                                                    18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 4
        (D) OTHER INFORMATION: /mod_base= OTHER
```

```
            /note= "N = thymidine modified by
            N,N,N',N'-tetramethyl-6-carboxyrhodamine
            through an aminohexylacrylimido linker"

(xi) SEQUENCE DESCRIPTION: SEQ ID NO:12:

NTTNTCCCAG TCACGACG                                                 18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by
            6-carboxy-X-rhodamine through an
            aminohexylacrylimido linker"

(xi) SEQUENCE DESCRIPTION: SEQ ID NO:13:

NTTNTCCCAG TCACGACG                                                 18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 5
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:14:

NTTTNCCCAG TCACGACG                                                 18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
    (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 5
         (D) OTHER INFORMATION: /mod_base= OTHER
             /note= "N = thymidine modified by
             2',7'-dimethoxy-4',5'-dichloro-6-
             carboxyfluorescein through an
             aminohexylacrylimido linker"

(xi) SEQUENCE DESCRIPTION: SEQ ID NO:15:

NTTTNCCCAG TCACGACG                                               18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 5
         (D) OTHER INFORMATION: /mod_base= OTHER
             /note= "N = thymidine modified by
             N,N,N',N'-tetramethyl-6-carboxyrhodamine
             through an aminohexylacrylimido linker"

(xi) SEQUENCE DESCRIPTION: SEQ ID NO:16:

NTTTNCCCAG TCACGACG                                               18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 5
         (D) OTHER INFORMATION: /mod_base= OTHER
             /note= "N = thymidine modified by
             6-carboxy-X-rhodamine through an
``` aminohexylacrylimido linker"

(xi) SEQUENCE DESCRIPTION: SEQ ID NO:17:

NTTTNCCCAG TCACGACG                                              18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 11
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:18:

NTTTTCCCAG NCACGACG                                              18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 11
        (D) OTHER INFORMATION: /mod_base= OTHER
            /note= "N = thymidine modified by
            2',7'-dimethoxy-4',5'-dichloro-6-
            carboxyfluorescein through an
            aminohexylacrylimido linker"

(xi) SEQUENCE DESCRIPTION: SEQ ID NO:19:

NTTTTCCCAG NCACGACG                                              18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA

```
    (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 11
         (D) OTHER INFORMATION: /mod_base= OTHER
             /note= "N = thymidine modified by
             N,N,N',N'-tetramethyl-6-carboxyrhodamine
             through an aminohexylacrylimido linker"

(xi) SEQUENCE DESCRIPTION: SEQ ID NO:20:

NTTTTCCCAG NCACGACG                                                18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 11
         (D) OTHER INFORMATION: /mod_base= OTHER
             /note= "N = thymidine modified by
             6-carboxy-X-rhodamine through an
             aminohexylacrylimido linker"

(xi) SEQUENCE DESCRIPTION: SEQ ID NO:21:

NTTTTCCCAG NCACGACG                                                18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = guanosine modified by
             5-carboxyfluorescein through an
             aminohexyl linker"

(ix) FEATURE:
         (A) NAME/KEY: modified_base
         (B) LOCATION: 4
         (D) OTHER INFORMATION: /mod_base= OTHER
             /note= "N = thymidine modified by an
             aminohexylacrylimide linker"

(xi) SEQUENCE DESCRIPTION: SEQ ID NO:22:
```

```
NTTNTCCCAG TCACGACG                                                 18
```

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = adenosine modified by
            5-carboxyfluorescein through an
            aminohexyl linker"

(ix) FEATURE:
        (A) NAME/KEY: modified_base
        (B) LOCATION: 11
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:23:

```
NTTCAAAGGG NATCTGGGCT CTGG                                          24
```

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 15
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:24:

```
NTGGGCTGAA AAGCNCCCGA TTAT                                          24
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1

(D) OTHER INFORMATION: /mod_base= OTHER
                /note= "N = adenosine modified by
                5-carboxyfluorescein through an
                aminohexyl linker"

(ix) FEATURE:
            (A) NAME/KEY: modified_base
            (B) LOCATION: 3
            (D) OTHER INFORMATION: /mod_base= OTHER
                /note= "N = thymidine modified by
                6-carboxy-X-rhodamine through an
                aminohexylacrylimido linker"

(xi) SEQUENCE DESCRIPTION: SEQ ID NO:25:

NTNCAAAGGG TATCTGGGCT CTGG                                              24

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                6-carboxyfluorescein through an
                aminohexyl linker"

(ix) FEATURE:
            (A) NAME/KEY: modified_base
            (B) LOCATION: 7
            (D) OTHER INFORMATION: /mod_base= OTHER
                /note= "N = thymidine modified by
                6-carboxy-X-rhodamine through an
                aminohexylacrylimido linker"

(xi) SEQUENCE DESCRIPTION: SEQ ID NO:26:

NTGGGCNGAA AAGCTCCCGA TTAT                                              24

(2) INFORMATION FOR SEQ ID NO:27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linker"

(ix) FEATURE:
            (A) NAME/KEY: modified_base
            (B) LOCATION: 7
            (D) OTHER INFORMATION: /mod_base= OTHER
                /note= "N = thymidine modified by an
                aminohexylacrylimide linker"

(xi) SEQUENCE DESCRIPTION: SEQ ID NO:27:

NTGGGCNGAA AAGCTCCCGA TTAT                                              24

```
(2) INFORMATION FOR SEQ ID NO:28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 9
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:28:

NAAAGCCCNA GTGGATGATA AGAATAAT                                    28

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GGACAGATGA TAAATACATA GGATGGATGG                                  30

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 7
        (D) OTHER INFORMATION: /mod_base= OTHER
            /note= "N = thymidine modified by
            5-carboxyfluorescein through an
            aminohexylacrylimido linker"

(xi) SEQUENCE DESCRIPTION: SEQ ID NO:30:

NTGGGCNGAA AAGCTCCCGA TTAT                                        24

(2) INFORMATION FOR SEQ ID NO:31:
```

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:31:

ATTCAAAGGG TATCTGGGGC TCTGG                                              25

(2) INFORMATION FOR SEQ ID NO:32:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
              /note= "N = guanosine modified by
              5-carboxyfluorescein through an
              aminohexyl linker"

(ix) FEATURE:
         (A) NAME/KEY: modified_base
         (B) LOCATION: 9
         (D) OTHER INFORMATION: /mod_base= OTHER
              /note= "N = thymidine modified by
              5-carboxyfluorescein through an
              aminohexylacrylimido linker"

(xi) SEQUENCE DESCRIPTION: SEQ ID NO:32:

NGAGGAACNG GGAACCACAC AGGT                                               24

(2) INFORMATION FOR SEQ ID NO:33:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:33:

ACTGGCACAG AACAGGCACT TAGG                                               24

(2) INFORMATION FOR SEQ ID NO:34:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
              /note= "N = adenosine modified by
              5-carboxyfluorescein through an
              aminohexyl linker"

(ix) FEATURE:
         (A) NAME/KEY: modified_base (B) LOCATION: 9
                (D) OTHER INFORMATION: /mod_base= OTHER
                    /note= "N = thymidine modified by
                    5-carboxyfluorescein through an
                    aminohexylacrylimido linker"

(xi) SEQUENCE DESCRIPTION: SEQ ID NO:34:

NACCTGAGNC TGCCAAGGAC TAGC                                                  24

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:35:

TTCCACACAC CACTGGCCAT CTTC                                                  24

(2) INFORMATION FOR SEQ ID NO:36:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linker"

(ix) FEATURE:
            (A) NAME/KEY: modified_base
            (B) LOCATION: 4
            (D) OTHER INFORMATION: /mod_base= OTHER
                /note= "N = thymidine modified by
                N,N,N',N'-tetramethyl-6-carboxyrhodamine
                through an aminohexylimido linker"

(xi) SEQUENCE DESCRIPTION: SEQ ID NO:36:

NTTNTCCCAG TC                                                               12

(2) INFORMATION FOR SEQ ID NO:37:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by
                5-carboxyfluorescein through an
                aminohexyl linker"

(ix) FEATURE:
            (A) NAME/KEY: modified_base
            (B) LOCATION: 4
            (D) OTHER INFORMATION: /mod_base= OTHER /note= "N = thymidine modified by
            aminohexylacrylimide linker"

(xi) SEQUENCE DESCRIPTION: SEQ ID NO:37:

NTTNTCCCAG TC                                                              12

(2) INFORMATION FOR SEQ ID NO:38:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 5
        (D) OTHER INFORMATION: /mod_base= OTHER
            /note= "N = thymidine modified by an
            aminohexylacrylimide linker"

(xi) SEQUENCE DESCRIPTION: SEQ ID NO:38:

NTTTNCCCAG TC                                                              12

(2) INFORMATION FOR SEQ ID NO:39:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 11
        (D) OTHER INFORMATION: /mod_base= OTHER
            /note= "N = thymidine modified by an
            aminohexylacrylimide linker"

(xi) SEQUENCE DESCRIPTION: SEQ ID NO:39:

NTTTTCCCAG NC                                                              12

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

```
GTGGGCTGAA AAGCTCCCGA TTAT                                                    24

(2) INFORMATION FOR SEQ ID NO:41:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

TATTGGGCGC CAGGGTGGTT TTTCTTTTCA CCAGTGAGAC GGGCAACA                           48

(2) INFORMATION FOR SEQ ID NO:42:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by
            5-carboxyfluorescein through an
            aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by
            N,N,N',N'-tetramethyl-6-carboxyrhodamine
            through an aminohexylacrylimido linker"

(xi) SEQUENCE DESCRIPTION: SEQ ID NO:42:

NTTNTCCCAG TC                                                                 12
```

PROBES LABELED WITH ENERGY TRANSFER COUPLED DYES

CROSS-REFERENCE TO RELATED APPLICATIONS

The following application is a continuation-in-part of application Ser. No. 08/411,573 filed Mar. 27, 1995 abandoned and application Ser. No. 08/410,808 filed Mar. 27, 1995 U.S. Pat. No. 5,707,804 which applications are both continuation-in-part applications of application Ser. No. 08/189,924 filed Feb. 1, 1994, U.S. Pat. No. 5,654,419 the disclosures of which are herein incorporated by reference.

INTRODUCTION

1. Technical Field

The field of this invention is fluorescent labeled primers and their use.

2. Background

There is an increasing demand to be able to identify and quantify components of mixtures. The greater the complexity of the mixture, the greater the interest in being able to simultaneously detect a plurality of the components present. As illustrative of this situation is DNA sequencing, where it is desirable to efficiently excite from one to four fluorescently tagged components with a laser source, while providing for fluorescent signal emission at a plurality of distinctive wavelengths, where the fluorescence signals should be as intense as possible. In this situation, the different labels should not adversely affect the electrophoretic mobility of the sequences to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15, 4593–4602 (1987); (2) the DNA fragments are labeled with four different fluorophores and all the fragments are electrophoretically separated and detected in a single lane (Smith et al., *Nature* 321, 674–679 (1986); (3) each of the dideoxynucleosides in the termination reaction is labeled with a different fluorophore and the four sets of fragments are run in the same lane (Prober et al., *Science* 238, 336–341 (1987); or (4) the sets of DNA fragments are labeled with two different fluorophores and the DNA sequences coded with the dye ratios (Huang et al., *Anal. Chem.* 64, 2149–2154 (1992).

All of these techniques have significant deficiencies. Method 1 has the potential problems of lane-to-lane variations in mobility, as well as a low throughput. Methods 2 and 3 require that the four dyes be well excited by one laser source and that they have distinctly different emission spectra. In practice, it is very difficult to find two or more dyes that can be efficiently excited with a single laser and that emit well separated and intense fluorescent signals.

As one selects dyes with distinctive red-shifted emission spectra, their absorption maxima will also move to the red and all the dyes can no longer be efficiently excited by the same laser source. Thus, the detection sensitivity for these dyes will suffer. Also, as more different dyes are selected, it becomes more difficult to select all the dyes such that they cause the same mobility shift of the labeled molecules.

It is therefore of continued interest that improved labels be developed which have strong absorption at a common wavelength, have a high quantum yield for fluorescence, have intense fluorescence signals and have a large Stokes shift of the emission.

Relevant Literature

U.S. Pat. No. 4,996,143 reports the preparation of oligonucleotide probes comprising donor and acceptor fluorophores designed for the detection of complementary DNA target sequences by hybridization to form labeled double-strand DNA fragments. These probes were specifically labeled in the middle of the probe, explicitly excluding the 5' or 3' end base unit.

Smith et al., Nucleic Acids Research (1986) 321:674–679 reports the synthesis of oligonucleotides having an aliphatic amino group at the 5' terminus, as well as the preparation of fluorescent derivatives thereof, containing only a single fluorescent label.

SUMMARY OF THE INVENTION

Labels comprising at least one pair of fluorophores, wherein a pair is comprised of a donor and acceptor fluorophore, in energy transfer relationship, and methods for their use, are provided. To generate the labels, pairs or families of fluorophores are bound to a backbone, particularly a nucleic acid backbone, where one member of the pair is bonded to a terminus of the backbone. The range of distances between donor and acceptor fluorophores is chosen to ensure efficient energy transfer, and can be modulated to affect the label mobility. The subject labels find particular use as primers in nucleotide chain extension applications, such as sequencing, PCR and the like.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 14 shows the comparison of signal strengths and mobility shifts of the single dye-labeled primers and ET primers. A total of eight sequencing reactions with ddTTP/dNTPs were run using 1 µg of M13mp18 DNA template and 0.4 pmol of primer and then loaded in 8 adjacent lanes of the ABI 373A sequencing gel. Panel A shows the raw traces obtained when single dye-labeled primers were used. Colors correspond to the dye as follows: blue, FAM; green, JOE; black, TAMRA; red, ROX. The region shown corresponds to the sequence approximately 15–35 bases from the 3' end of the primer. Panel B shows raw traces on identical scales obtained using ET primers. Colors correspond to the dye as follows: blue, F10F; green, F10J; black, F3T; red, F3R. Panels C and D display data from 4-color sequencing reactions run with single-dye primers (C) and ET primers (D) on identical scales. For reference, the ET primer data in (D) is also shown in analyzed format in panel E (SEQ ID NO:41). The reactions used for panel C included 0.4 pmol of FAM and JOE primer; 0.8 pmol of TAMRA and ROX primer, and the reactions for panel D and E included 0.4 pmol of each ET primer and a total of 6 µg of M13mp18 template DNA.

FIG. 23. Structures of the PCR primers (SEQ ID NOs:28–35 and 21) used for the amplification of the VWFA, THO1, TPO and CSF loci. The fluorescent primers are labeled with a common fluorescein donor (F) at the 5' end and either a second fluorescein or a rhodamine (R) acceptor at the indicated locations of a modified T in the sequence. The number of nucleotides between the two fluorophores is indicated in the primer designation.

DESCRIPTION OF SPECIFIC EMBODIMENTS

Figure 1:
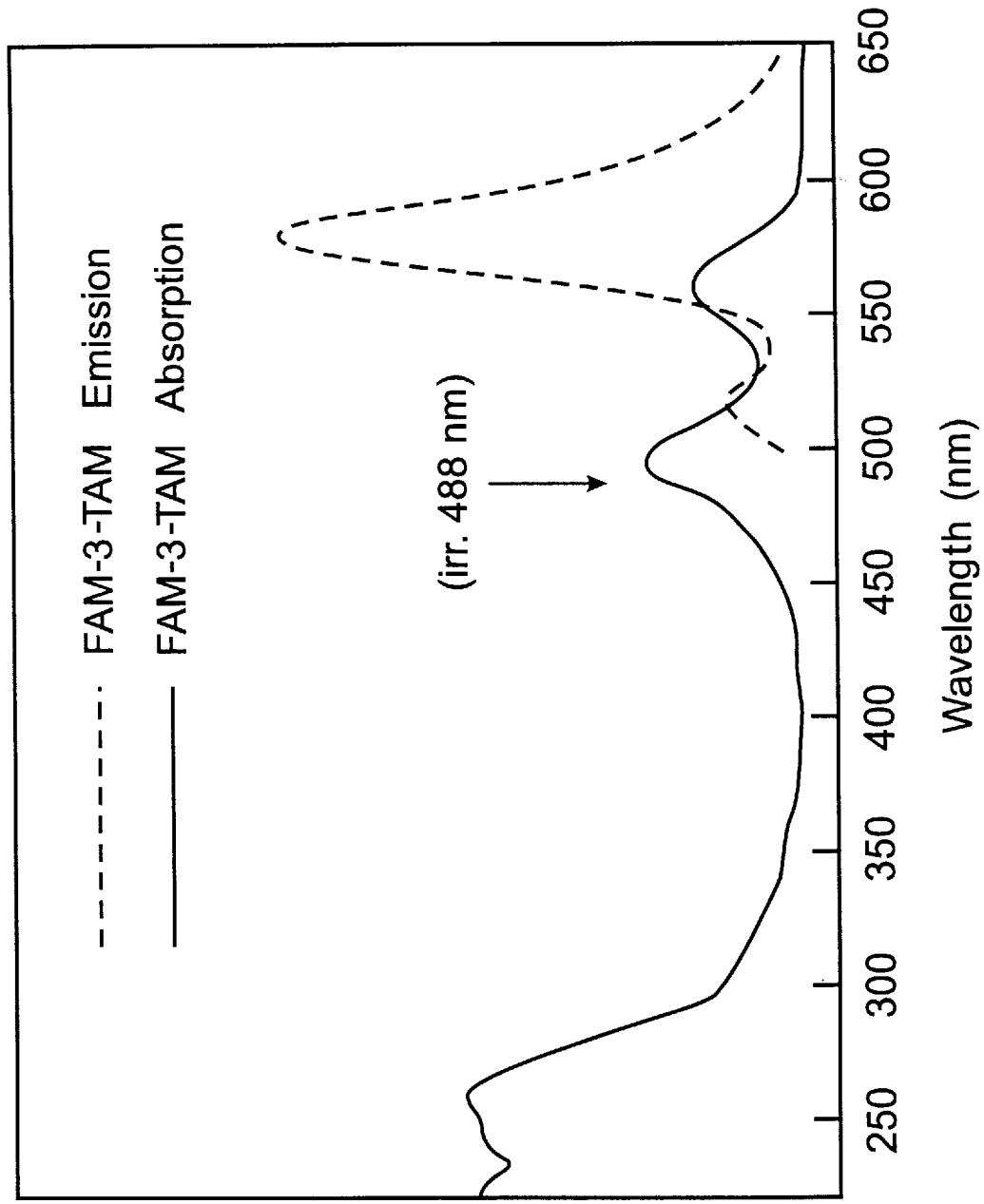
FIG. 1 is a graph of the absorption and emission spectra of FAM-3-TAM in 1×TBE.

Novel fluorescent labels, combinations of fluorescent labels, and methods of their use, are provided. The subject fluorescent labels comprise at least one donor and acceptor fluorophore, which may be the same or different, bound to a polymeric backbone in energy transfer relationship, where one of the fluorophores is positioned at one of the termini of the polymeric backbone. The range of distances between donor and acceptor fluorophores is chosen to ensure efficient energy transfer, and can be modulated to affect the label mobility. In the case where the fluorophores are identical, the range of distances is chosen so as to maximize the fluorescence intensity. The subject labels find particular use as primers in nucleotide chain extension applications, such as sequencing, PCR and the like.

The subject labels will comprise one or more pairs of fluorophores, where a donor and acceptor fluorophore make a pair. With one exception where the fluorophores are the same, the pair or pairs of fluorophores have overlapping spectra, where the donor emission overlaps the acceptor absorption, so that there is energy transfer from the donor to acceptor fluorophore. It is not essential that the excited or donor fluorophore actually fluoresce, it being sufficient that the excited fluorophore be able to efficiently absorb the excitation energy and efficiently transfer it to the emitting or acceptor fluorophore.

The donor fluorophores in the different families of fluorophores may be the same or different, but will be able to be excited efficiently by a narrow bandwidth source. The emitting or accepting fluorophores will be selected to be able to receive the energy from donor fluorophores and emit light, which will be distinctive and detectably different. Therefore, one will be able to distinguish between the components of the mixture to which the different labels have been bound.

Usually the donor fluorophores will absorb in the range of about 350–800 nm, more usually in the range of about 350–600 nm or 500–750 nm, while the acceptor fluorophores will emit light in the range of about 450–1000 nm, usually in the range of about 450–800 nm. One may have more than a pair of absorbing molecules, so that one may have 3 or more molecules, where energy is transferred from one molecule to the next at higher wavelengths, to greatly increase the difference in wavelength between absorption and observed emission.

The fluorophores may be selected so as to be from a similar chemical family, such as cyanine dyes, xanthenes or the like. Thus, one could have the donors from the same chemical family, each donor-acceptor pair from the same chemical family or each acceptor from the same family.

Among the members of the pairs of the fluorophores, one of the fluorophore members will be located at one of the termini of the label, with the other member or members being located at an internal site along the polymeric backbone of the label. In other words, either the donor or acceptor fluorophore may be located at one terminus of polymeric backbone while the other fluorophore member of the pair will be bonded to a non-terminal monomeric unit of the polymeric backbone. Thus, where the donor is bonded to one of the label termini, the acceptor will be bonded at an internal site along the polymeric backbone of the label, and vice versa where the acceptor is bonded to one of the label termini.

In the subject labels, the two fluorophores will be bonded to a backbone or chain, usually a polymeric chain, where the distance between the two fluorophores may be varied. As mentioned above, the distance between the donor and acceptor members of the pair will provide for efficient transfer of energy from the donor to the acceptor. In terms of monomeric units of the polymeric backbone chain, the distance between the pairs of fluorophores will be at least about 2, usually at least about 3, and may be as great as 10 or greater, but will usually be less than about 20, more usually less than about 15.

Various chains or backbones may be employed, where the backbones will comprise monomeric units having bases selected from purines, pyrimidines and hybridizing analogues thereof, such as nucleic acids, both DNA and RNA, modified nucleic acids, e.g. where oxygens may be substituted by sulfur, carbon, or nitrogen, phosphates substituted by sulfate or carboxylate, etc., polypeptides, e.g. peptide nucleic acids (Nielsen et al., Science (1991) 254:1497–1500; Hanvey et al., Science (1992) 258: 1481–1485), polysaccharides, various groups which may be added stepwise, such as di-functional groups, e.g. haloamines, or the like. The fluorophores may be substituted as desired by appropriate functionalization of the various building blocks, where the fluorophore may be present on the building block during the formation of the label, or may be added subsequently, as appropriate. Various conventional chemistries may be employed to ensure that the appropriate spacing between the two fluorophores is obtained.

It is found that the spacing between the two fluorophores will affect the mobility of the label. Therefore, one can use different dye pairs and, by varying the distance between the different dye pairs within a range which still permits good energy transfer, provide for substantially constant mobility for the labels. The mobility is not related to the specific spacing, so that one will empirically determine the effect of the spacing on the mobility of a particular label. However, because of the flexibility in the spacing of the fluorophores in the labels, by synthesizing a few different labels with different spacings and different dye pairs, one can now provide for a family of fluorescent labels, which share a common excitation, that have strong and distinctive emission and a substantially common mobility. Usually, the mobility will differ by not more than about 20% of each other, preferably not more than about 10% of each other, and more preferably within about 5% of each other, when used in a particular separation. The mobility may usually be determined by carrying out the separation of the labels by themselves or the labels bound to a common molecule which is relevant to the particular separation, e.g. a nucleic acid molecule of the appropriate size, where one is interested in sequencing. Relative mobility shift can also be adjusted by changing the dyes or dye derivatives used as donors and acceptors.

As discussed above, a wide variety of fluorescent dyes may find application as the fluorophores in the subject labels. These dyes will fall into various classes, where combinations of dyes may be used within the same class or between different classes. Included among the classes are dyes such as the xanthene dyes, e.g. fluoresceins and rhodamines; coumarins, e.g. umbelliferone; benzimide dyes, e.g. Hoechst 33258, phenanthridine dyes; e.g. Texas Red and ethidium dyes; acridine dyes; Bodipy; cyanine dyes, such as thiazole orange, thiazole blue, Cy 5, and Cyfr; carbazole dyes; phenoxazine dyes; porphyrin dyes; quinoline dyes; or the like. Thus, the dyes may absorb in the ultraviolet, visible or infra-red ranges. For the most part, the fluorescent molecules will have a molecular weight of less than about 2 kDal, generally less than about 1.5 kDal.

The energy donor should have strong molar absorbance coefficient at the desired excitation wavelength, desirably greater than about $10^4$, preferably greater than about $10^5$ $cm^{-1}M^{-1}$. The excitation maximum of the donor and the emission maximum of the acceptor (fluorescer) will be separated by at least 15 nm or greater. The spectral overlap integral between the emission spectrum of the donor chromophore and the absorption spectrum of the acceptor chromophore and the distance between the chromophores will be such that the efficiency of energy transfer from donor to acceptor will range from 20% to 100%.

Separation of the donor and acceptor based on number of atoms in the chain will vary depending on the nature of the backbone, whether rigid or flexible, involving ring structures or non-cyclic structures or the like. Generally the number of atoms in the chain (the atoms in the ring structures will be counted as the lowest number of atoms around one side of the ring for inclusion in the chain) will be below about 200, usually below about 150 atoms, preferably below about 100, where the nature of the backbone will influence the efficiency of energy transfer between donor and acceptor.

While for the most part, pairs of fluorophores will be used, there can be situations where up to four different, usually not more than three different, fluorophores bound to the same backbone may find use. By using more fluorophores, one may greatly extend the Stokes shift, so that one may excite in the visible wavelength range and emit in the infra-red wavelength range, usually below about 1000 nm, more usually below about 900 nm. Detecting light in the infra-red wavelength range has many advantages, since it will not be subject to interference from Raman and Rayleigh light resulting from the excitation light. In order to maintain the mobility constant, one may use the same number of fluorophores on the labels, having a multiplicity of the same fluorophore to match the number of fluorophores on labels having different fluorophores for the large Stokes shift.

Of particular interest are labels comprising a donor and acceptor fluorophore bonded to a nucleic acid backbone, where the labels will generally have at least about 10 nucleotides and not more than about 50 nucleotides, usually not more than about 30 nucleotides. In these particular labels, one of the fluorophores (the first fluorophore), where the first fluorophore may be either the donor or acceptor fluorophore, will be bonded to the 5' terminus of the label, with the other fluorophore(s) being bonded to an internal nucleotide 3' to the first fluorophore, where the number of the liucleotides between the donor and acceptor fluorophores will range from about 2 to 15, usually from about 3 to 10 and more usually from about 4 to 10.

The fluorophores will usually be joined to the nucleotides by a convenient linking arm of from about 2 to 20, usually 4 to 16 atoms in the chain. The chain may have a plurality of functionalities, particularly non-oxo-carbonyl, more particularly ester and amide, amino, oxy, and the like. The chain may be aliphatic, alicyclic, aromatic, heterocyclic, or combinations thereof, usually comprising carbon, nitrogen, oxygen, sulfur, or the like in the chain.

For the most part the fluorophores will have maximum emission wavelengths that differ by 100 nm or less, where the maximum emission wavelengths of the donor and acceptor fluorophores will typically differ by at least about 10 nm, usually at least about 15 nm, more usually at least about 20 nm, but will generally differ by less than about 100 nm, usually less than about 25 nm.

For the subject labels, the donor and acceptor fluorophores are diawn from classes of compounds such as phenylxanthene dyes, cyanine dyes, phenanthridine dyes, aminonaphthylimide derivatives, and the like. Of particular interest is FAM as a common donor with JOE, TAMRA, ROX, 6-carboxyrhodamine-6G, or 5-carboxyrhodamine-6G as alternative acceptors in donor/acceptor pairs. Under some conditions, e.g. where it is desired that the excitation wavelength closely correlate to the maximum absorption wavelength of the donor molecule, cyanine donors may be preferred.

The subject labels may be prepared using any convenient means. A large number of nucleosides are available, which are functionalized, and may be used in the synthesis of a polynucleotide. By synthesizing the subject nucleic acid labels, one can define the specific sites at which the fluorophores are present. Commercially available synthesizers may be employed in accordance with conventional ways, so that any sequence can be achieved, with the pair of fluorophores having the appropriate spacing.

The subject labels find use in a variety of applications, including various separation techniques, such as electrophoresis, chromatography, or the like, where one wishes to have optimized spectroscopic properties, high sensitivity and comparable influence of the labels on the migratory aptitude of the components being analyzed. Of particular interest is electrophoresis, such as gel, capillary, etc. Among chromatographic techniques are HPLC, affinity chromatography, thin layer chromatography, paper chromatography, and the like.

The subject labels wherein the polymeric backbone is a nucleic acid chain find particular use as primers in nucleic acid chain extension applications, including sequencing, the polymerase chain reaction, particularly for sizing, or other systems where primers are employed for nucleic acid extension and one wishes to distinguish between various components of the mixture as related to the particular labels.

In sequencing, universal primers may be employed, where a different pair of fluorophores are used for each of the different dideoxynucleosides used for the extension during sequencing. In other words, universal primers may be prepared, where the primer may be any one of the universal primers, having been modified by bonding of the two fluorophores to the primer. Thus, various commercial primers are available, such as primers from pUC/M13, λgt10, λgt11, and the like. See, Sambrook et al., *Molecular Cloning: A Laboratory Manual*, 2nd ed., CSHL, 1989, Section 13. DNA sequences are cloned in an appropriate vector having a primer sequence joined to the sequence to be sequenced. Different 2', 3' ddNTPs are employed, so that termination occurs at different sites, depending upon the particular ddNTP which is present in the chain extension. By employing the subject primers, each ddNTP will be associated with a particular label. After extension with the Klenow fragment, the resulting fragments may then be separated in a single lane by electrophoresis or in a single capillary by electrophoresis, where one can detect the terminating nucleotide by virtue of the fluorescence of the label.

With PCR, where different primers have been used in PCR, each of the primers may be labeled in accordance with the subject invention, so that one can readily detect the presence of the target sequence complementary to each of the different primers. For example, the subject labels may used with the rapid sizing of alleles, as exemplified by short tandem repeat (STR) alleles, or other sequences where one wishes to detect small base or base pair differences, such as small differences of as few as a single base or base pair. By using the subject labels in conjunction with capillary electrophoresis, particularly capillary array electrophoresis, and employing an intercalating agent in the buffer, separations differing by one base may be achieved. The method can be used with dsDNA, particularly dsDNA obtained using the polymerase chain reaction or the ligase chain reaction, where the subject labels may be used as primers. One or both of the primers for the amplification may be labels, where the fluorophore pairs may be the same or different, depending on the needs of the separation. The intercalating agents may be fluorescent or non-fluorescent, such as thiazole orange, 9-aminoacridine, ethidium bromide, and the like, but for the specific example give here they are preferably non-fluorescent. Concentrations will generally be in the range of 0.1 to 10 μM. Conventional conditions may be used for the capillary electrophoresis, using a polyacrylamide wall coating and, for example, using hydroxyethylcellulose at from about 0.5 to 1% in an appropriate running buffer. Voltages may vary from about 50 to 150 V/cm or larger. The amount of DNA will generally be in the range of about 1 pg/μl to 1 ng/μl, although greater or lesser amounts may be used. Obviously, such method can also be used for single strand (ss) DNA fragment analysis to detect the labeled ssDNA fragments by virtue of their fluorescence, using linear polytcrylamide or the like in CE, which permits single base resolution.

The subject labels also find use with non-denaturing separation matrices to analyze ds-DNA PCR fragments and STR's, where the use of the subject labels overcomes the disadvantages of nondenaturing separation matrices in such applications, including problems with: single base-pair resolution, the identification of single base insertion/deletion variants, the appearance of extra peaks due to the formation of heteroduplex structures which leads to difficulties in interpretation and multiplexing, and the like. For example, accurate multiplexed STR sizing is routinely achieved using non-denaturing, replaceable sieving matrices and an M13 A-termination ladder as the standard by employing multiplexed STR samples that are amplified with the subject labels, where the subject labels are detected in the green channel and the M13 A-extension produced with a label according to the subject invention is detected in the red channel. The use of the subject labels in such applications provides for separations that are as fast as those achieved under native conditions, with single base resolution and an absence of interference from heteroduplex structures.

Kits are provided having combinations of labels, usually at least 2. Each of the labels will have the acceptor-donor pair, usually with comparable backbones, where the labels will be separated along the backbone to give comparable mobility in the separation method to be used. Each of the labels in a group to be used together will absorb at about the same wavelength and emit at different wavelengths. Each of the labels in the group will have about the same effect on mobility in the separation method, as a result of the variation in placement of the different fluorophores along the backbone.

The kits will generally have up to about 6, usually about up to about 4 different labels which are matching, but may have 2 or more sets of matching labels, having 2–6 different labels.

Of particular interest are labels comprising a nucleic acid backbone, where the labels may be present on the nucleotides which hybridize to the complementary sequence or may be separated from those nucleotides. The entire nucleic acid sequence may be complementary to the 5' primer sequence or may be complementary only to the 3' portion of the sequence. Usually, there will be at least about 5 nucleotides, more usually at least about 8 nucleotides which are complementary to the sequence to be copied. The primers are combined with the sequence to be copied in the appropriate plasmid having the primer sequence at the 3' end of the strand to be copied and dNTPs added with a small amount of the appropriate ddNTP. After extension, the DNA may be isolated and transferred to a gel or capillary for separation.

The kits which are employed will have at least two of the subject labels, which will be matched by having substantially the same absorption for the donor molecule, distinct emission spectra and substantially the same mobility. Generally for single stranded nucleic acids, the separation will be from about 1–15, more usually 1–12, preferably about 2–10 nucleosides between fluorophores.

The following examples are offered by way of illustration and not by way of limitation.

EXPERIMENTAL

I. Preparation of Energy Transfer Fluorescent Dye Labels

A. Design and Synthesis of Energy Transfer Fluorescent Dye Tagged Oligonucleotide Labels Deoxyoligonucleotides (12-base long) with the sequence 5'-GTTTTCCCAGTC-3', (SEQ ID NO: 1) selected from the M13 universal primer, were synthesized with donor-acceptor fluorophore pairs separated by different distances. Specifically, the 12-mer contains a modified base introduced by the use of 5'dimethoxytrityl-5-[N-(trifluoroacetylaminohexy)-3-acrylimido]-2'-deoxyUridine, 3'-[(2-cyanoethyl)-(N,N-diisopropyl)]-phosphoramidite (Amino-Modifier C6 dT) (Structure 1), which has a primary amine linker arm at the C-5 position.

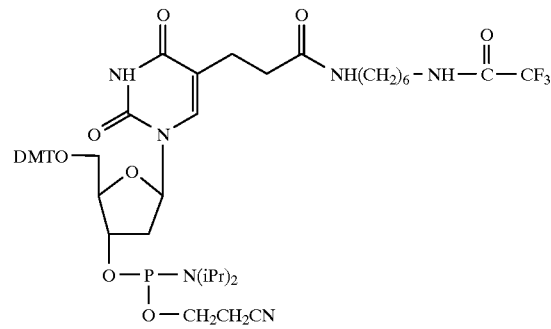

Structure 1. Amino-Modifier C6 dT

The donor dye was attached to the 5' side of the oligomer, and the acceptor dye was attached to the primary amine group on the modified T. The distances between the donor and acceptor were changed by varying the position of the modified T on the oligomer. The primers are denoted as D—N—A, where D is the donor, A is the acceptor and N is the number of bases between D and A. In all the primers prepared, D is Applied Biosystems Inc. ("ABI") dye FAM, a fluorescein derivative, A is ABI dyes TAM or ROX which are both rhodamine derivatives, or JOE, a fluorescein derivative. As a representative example, the structure of FAM-3-TAM is shown below (Structure 2).

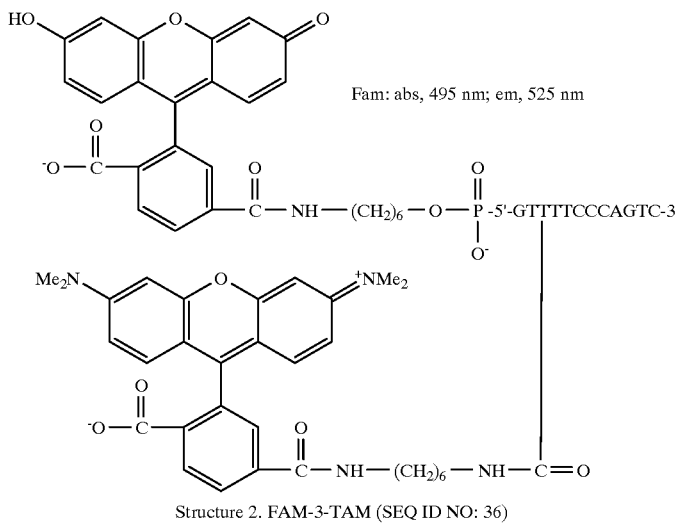

Structure 2. FAM-3-TAM (SEQ ID NO: 36)

Figure 2:
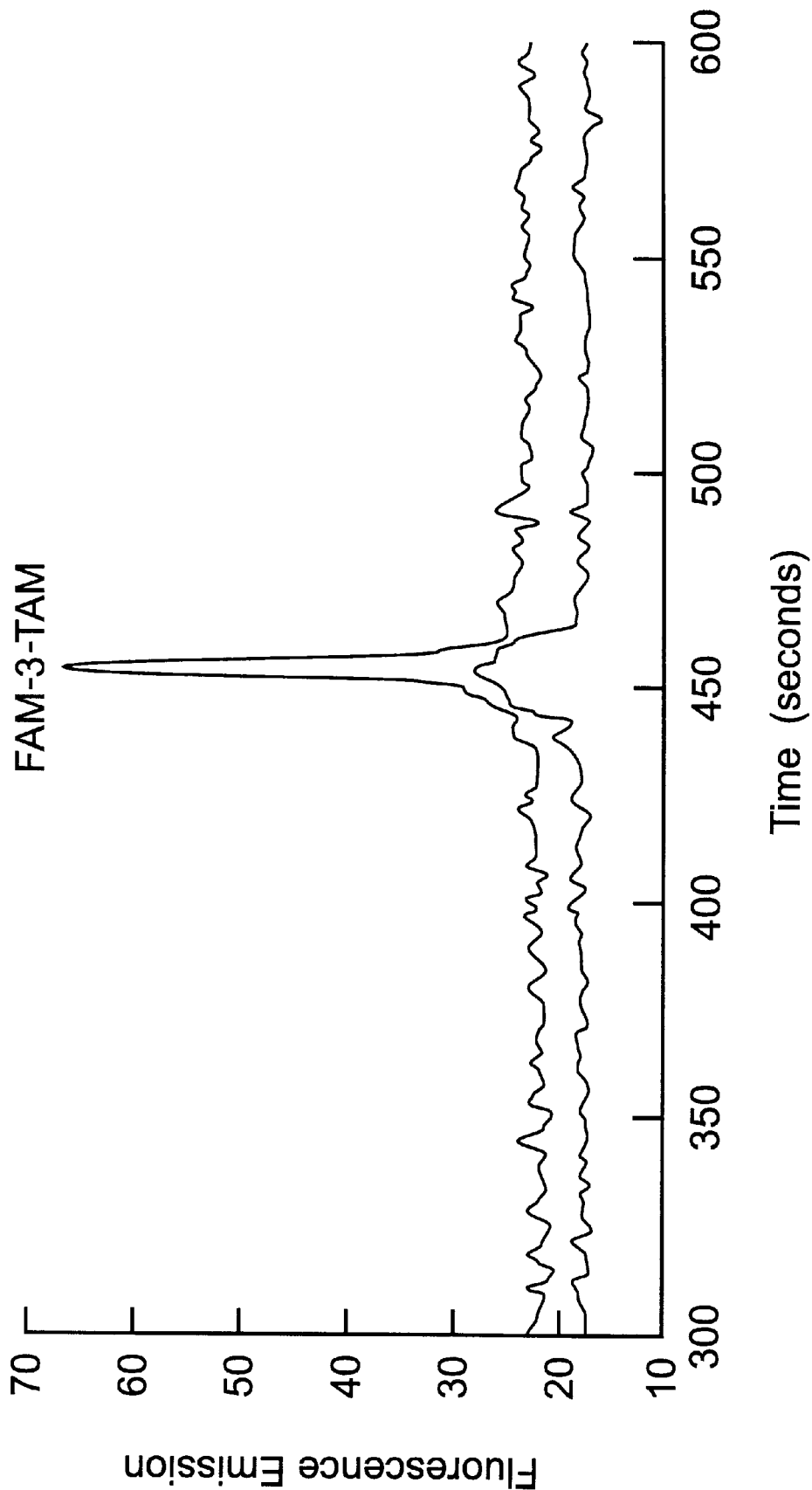
FIG. 2 is a CE (capillary electrophoresis) electropherogram of FAM-3-TAM. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 3:
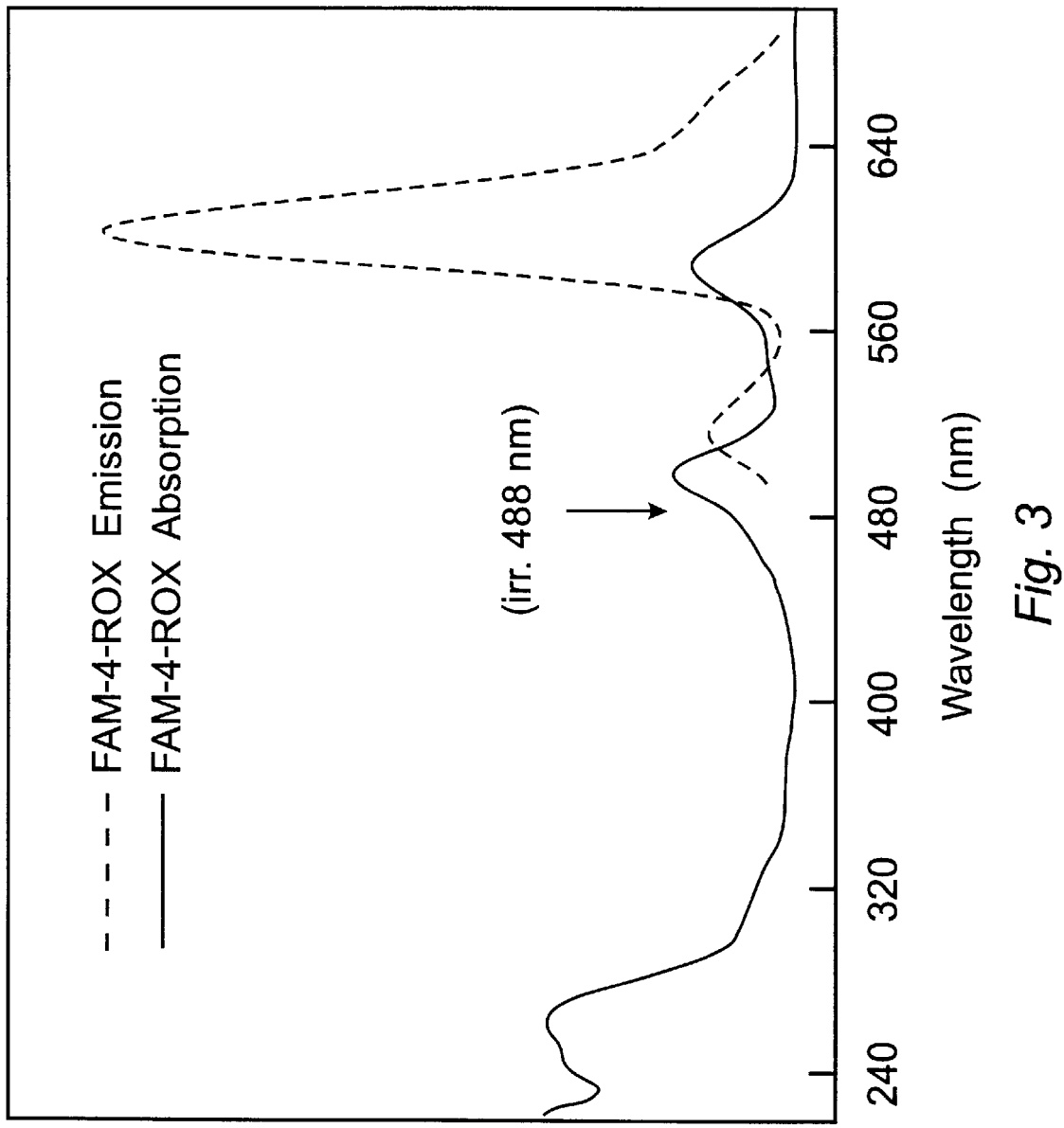
FIG. 3 is a graph of the absorption and emission spectra of FAM-4-ROX in 1×TBE.
Figure 4:
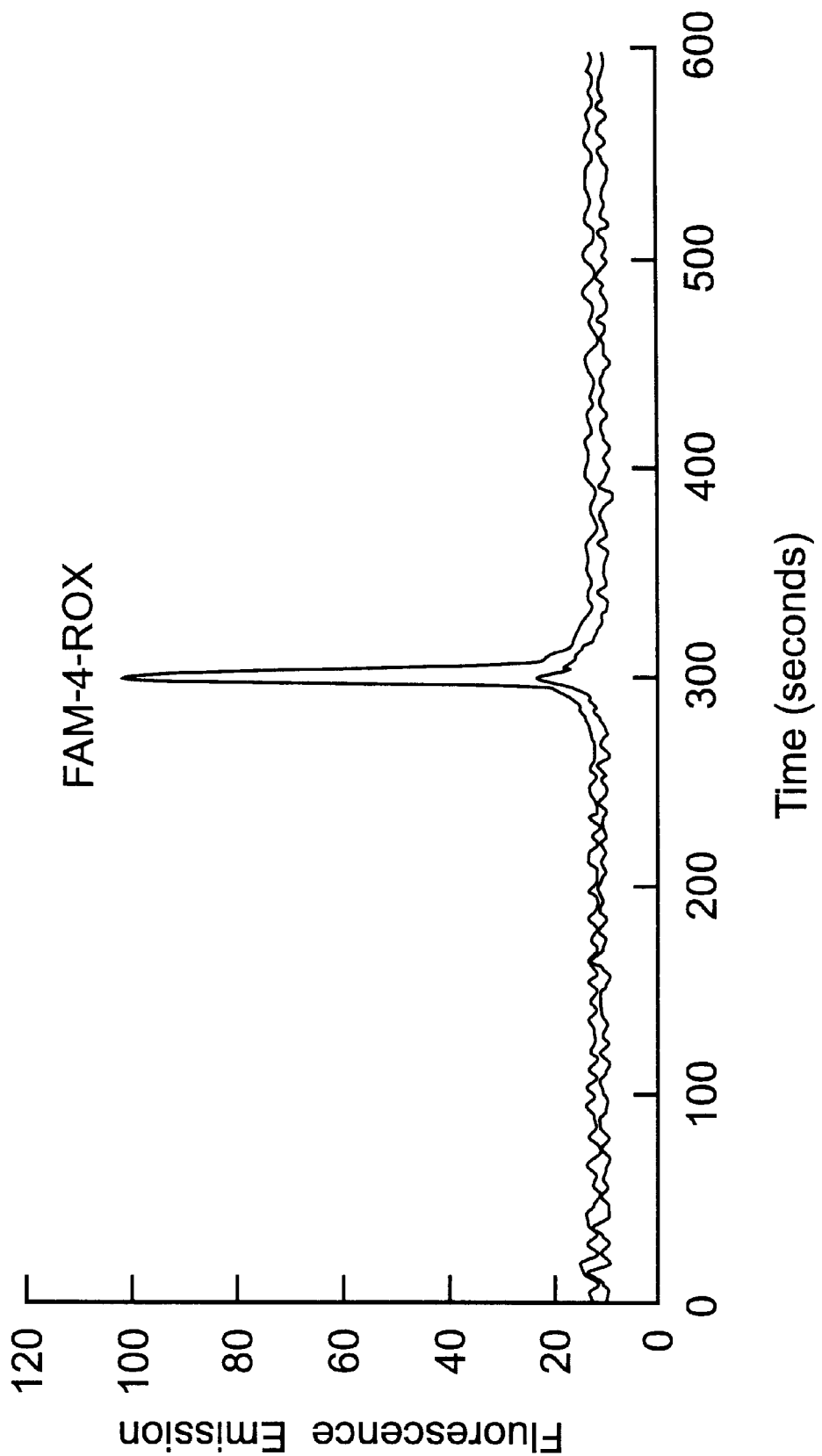
FIG. 4 is a CE electropherogram of FAM-4-ROX. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 5:
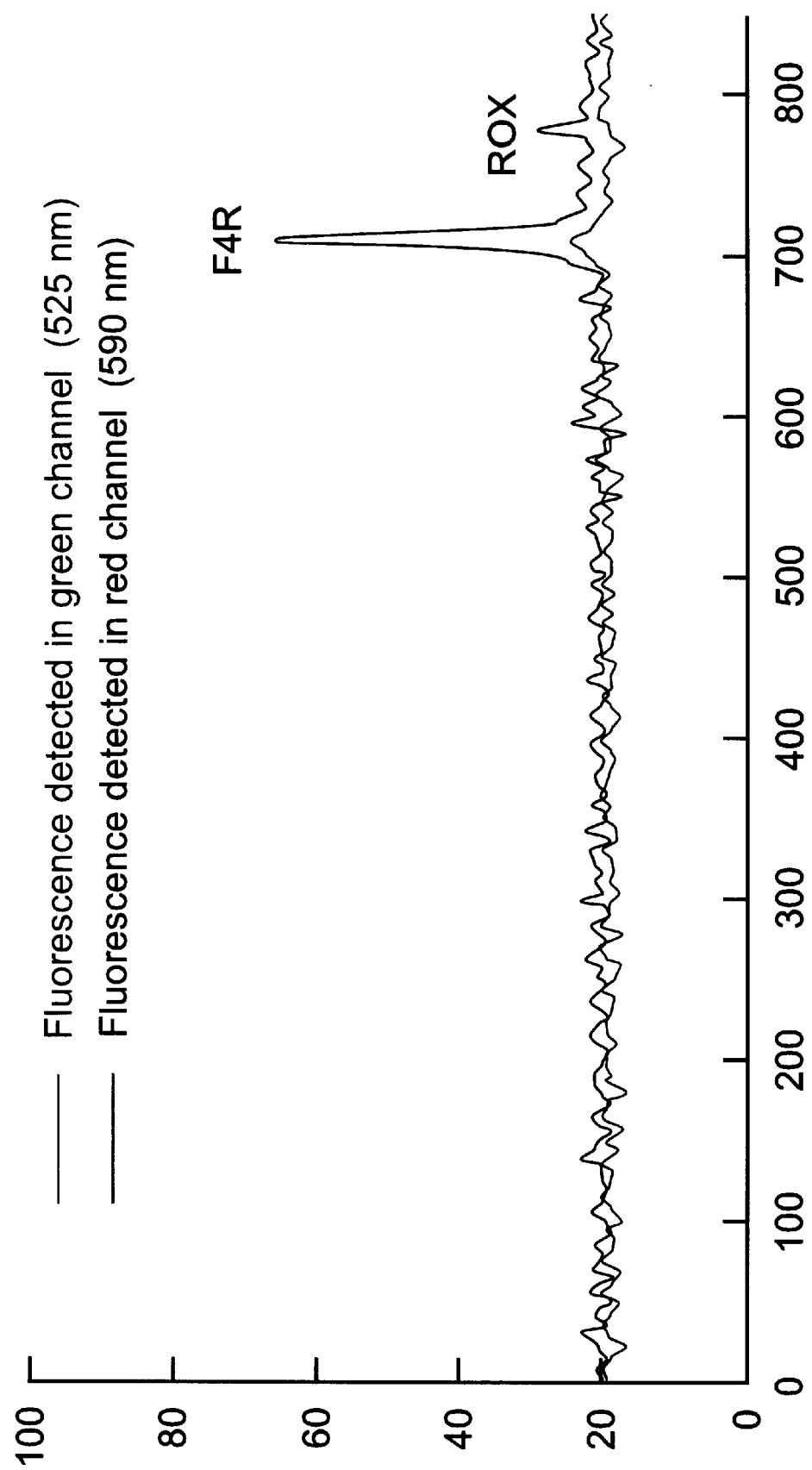
FIG. 5 is a CE electropherogram of FAM-4-ROX and ROX primner. The two primers at the same concentration were mixed together in 80% formamide and injected into the capillary. The fluorescence signals were detected in the green and red channels simultaneously with 476 nm excitation.

The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. The visible spectrum of FAM-3-TAM has both the absorption of FAM (495 nm) and TAM (560 nm); however with excitation at 488 nm nearly all of the emission comes out from T with a maximum at 579 nm (FIG. 1). This demonstrates efficient fluorescence energy transfer from FAM to TAM. This can also be seen by running the primer down a capillary electrophoresis (CE) column and detecting in red and green channels. With a FAM- and TAM-labeled primer, nearly all the emission is seen in the red channel (590 nm) (FIG. 2), indicating that the energy from donor FAM was transferred almost completely to the acceptor TAM, producing a Stokes shift of 91 nm. The observation of a single peak indicates the primer is pure. The same outcome is seen for FAM-4-ROX, which gives even a larger Stokes shift of 114 nm (FIGS. 3 and 4). Enhancement of the fluorescence signals of the energy transfer primers compared to single dye labeled primer is seen, where an ABI ROX primer at the same concentration as that of FAM-4-ROX (measured by UV) was injected in the same capillary. The resulting fluorescence signal of FAM-4-ROX is seen to be more than ten times higher than that of the ROX primer (FIG. 5).

Figure 6:
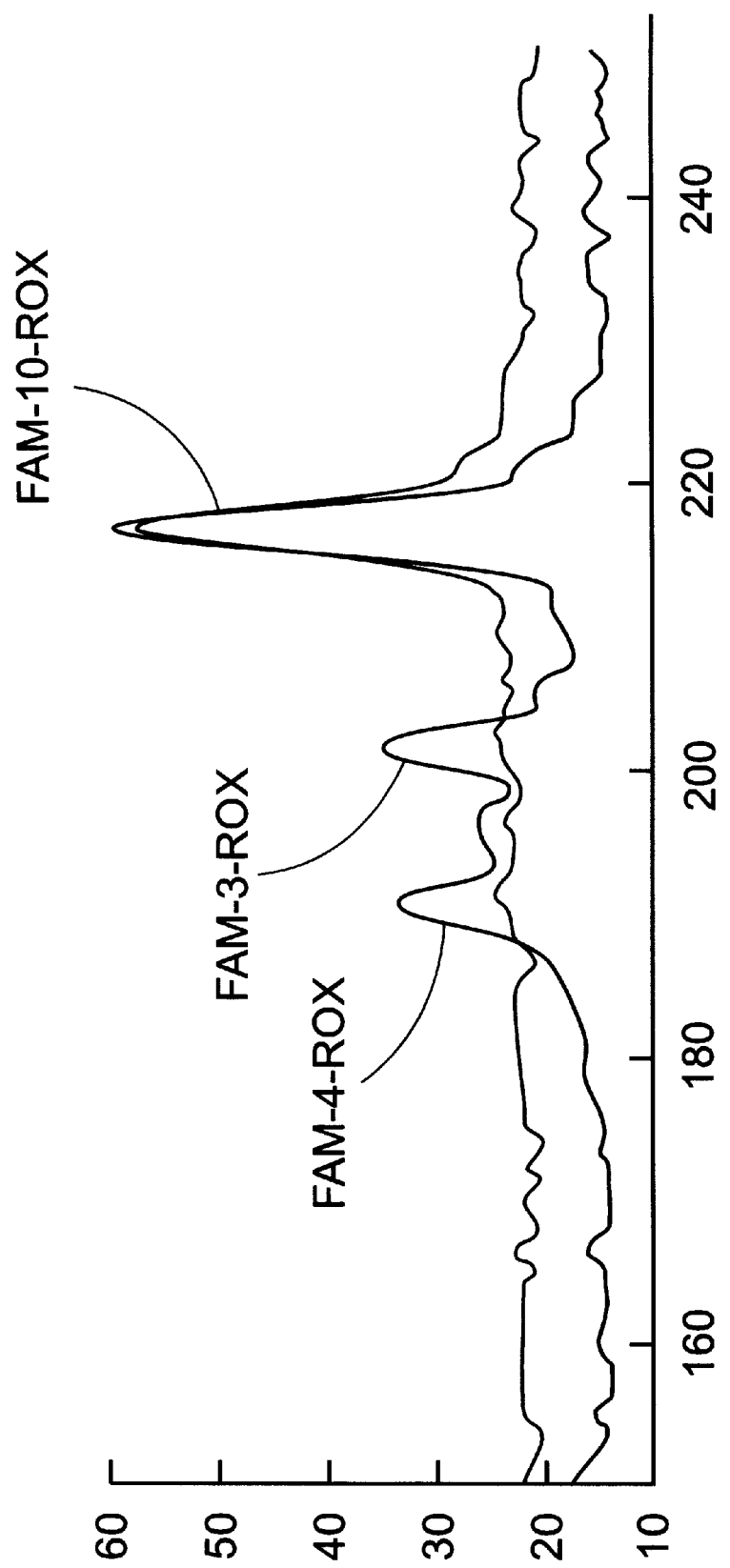
FIG. 6 is a CE electropherogram of a FAM-3-ROX, FAM-4-ROX and FAM-10-ROX mixture, showing the dependence of the mobility on the distance, between the donor and acceptor. The sample was analyzed by typical capillary electrophoresis DNA sequencing conditions with 488 nm excitation; and emission at 525 nm (green channel) and 590 nm (red channel).
Figure 7:
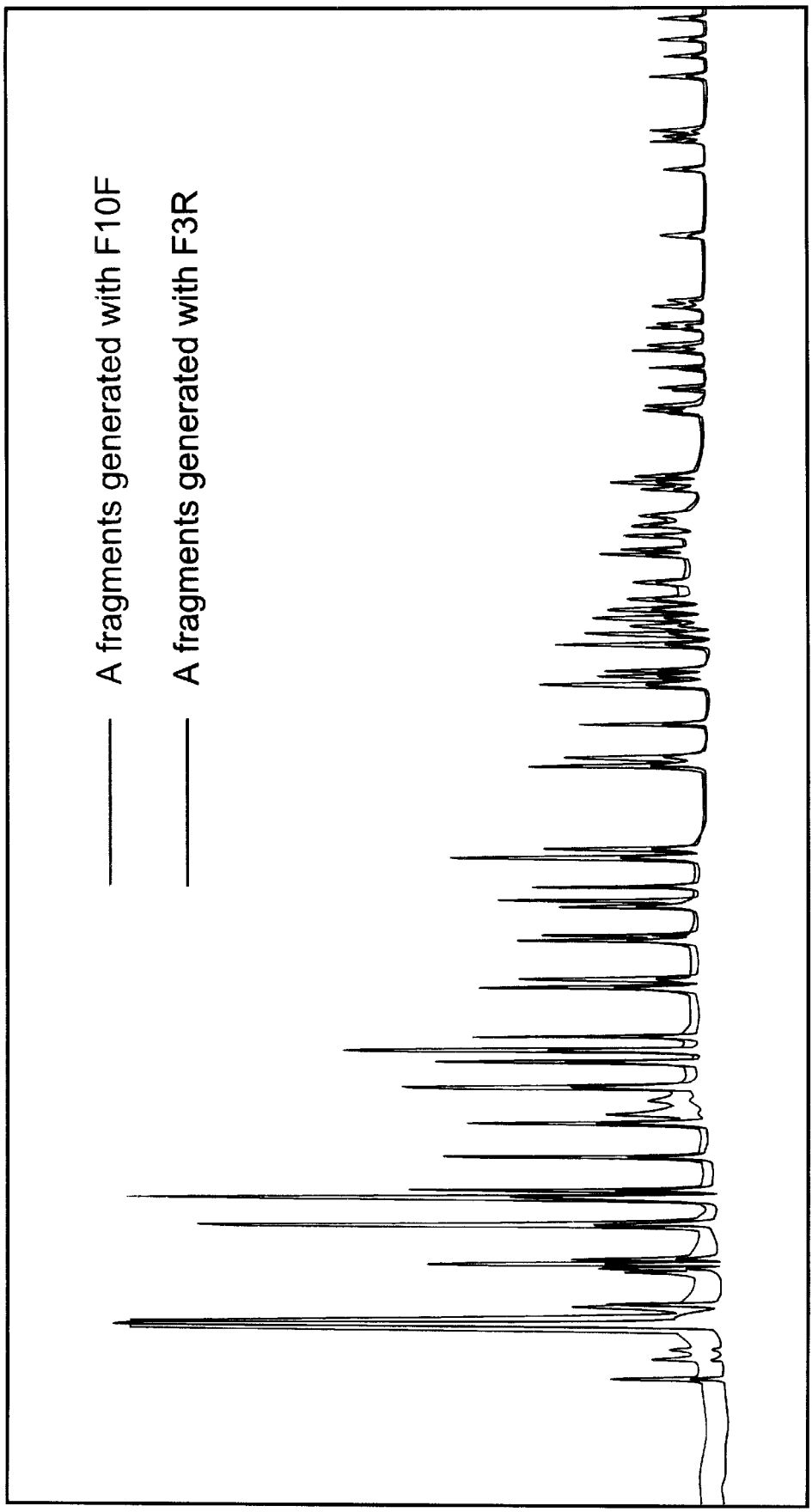
FIG. 7 is a comparison of the mobility shift of different dye primers on M13 mp 18 A fragment DNA samples.
Figure 8A:
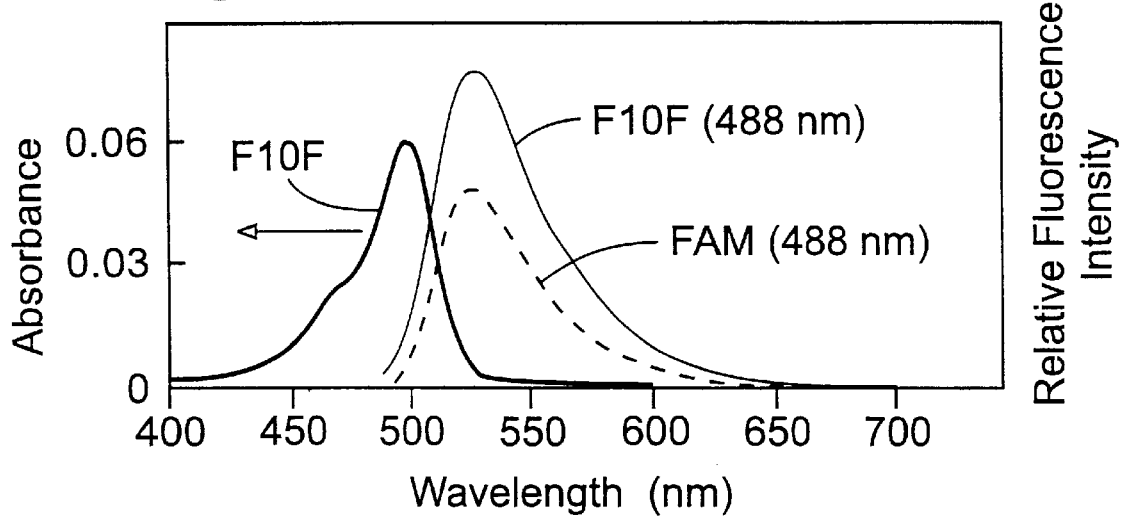
FIG. 8 shows the comparison of the fluorescence emission intensity of the four energy transfer (ET) primers (F10F, F10J, F3T and F3R) with the corresponding single dye-labeled primers at the indicated excitation wavelength (1×TBE, 7M urea). The thick lines indicate the absorption spectra of the ET primers. (A) F10F vs. FAM, (B) F10J vs. JOE, (C) F3T vs. TAMRA and (D) F3R vs. ROX. The emission spectra for each primer pair were determined using solution having the same molar concentration.
Figure 8B:
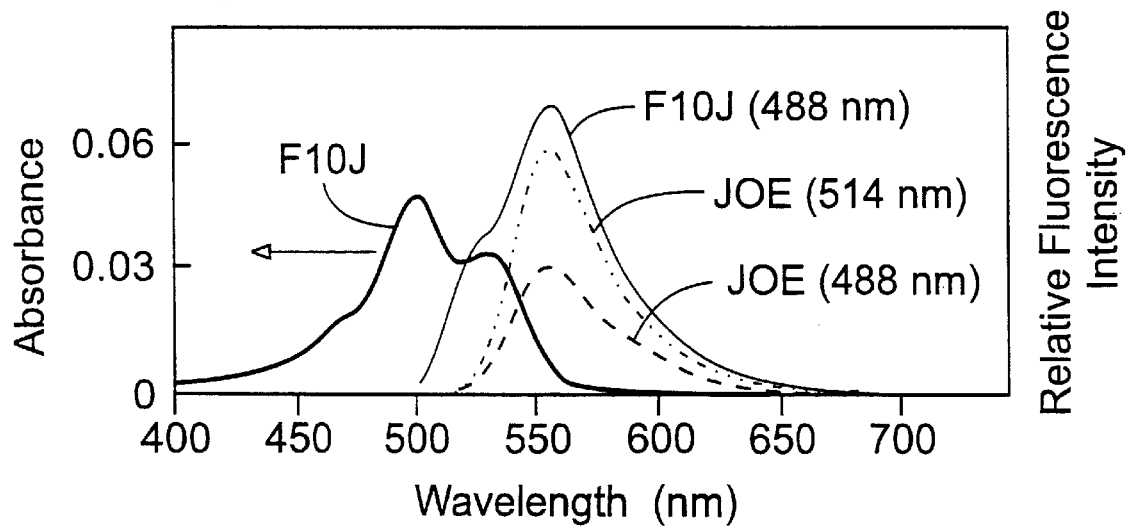
Figure 8C:
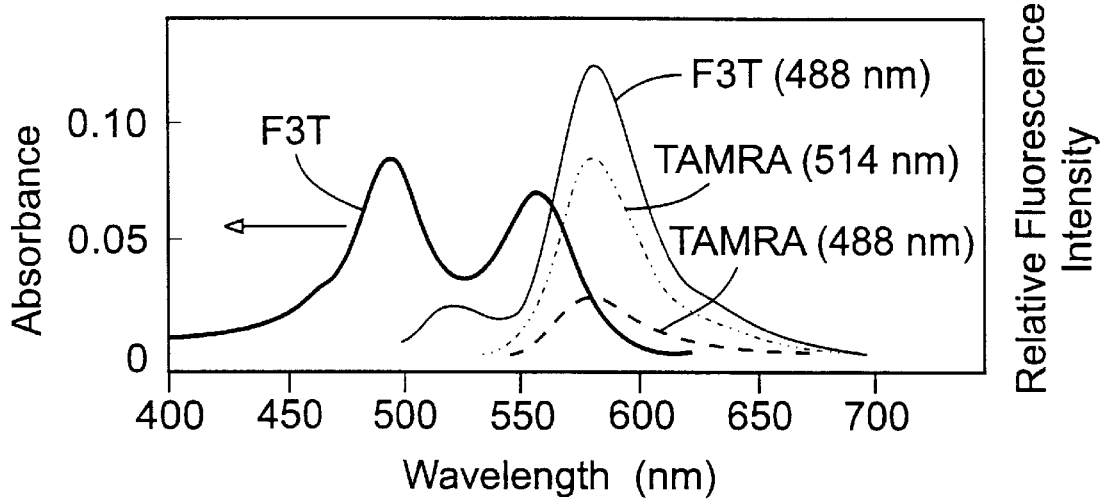
Figure 8D:
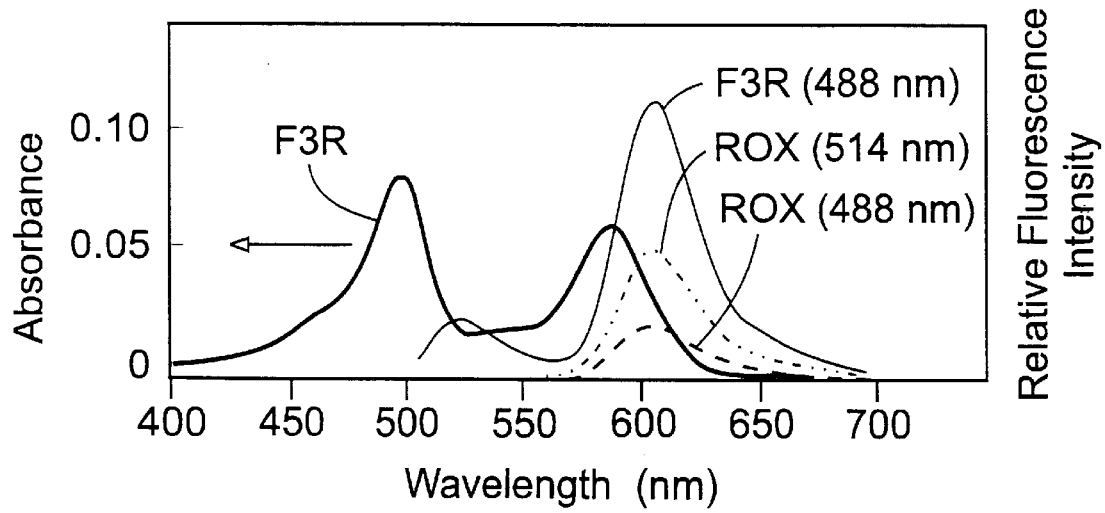

For the successful application of donor-acceptor fluorophore labeled primers to DNA sequencing, it is advantageous that the primers produce the same mobility shifts of the DNA fragments and display distinct fluorescence signals. It was found that the mobility of the primers depends on the distance between the donor and acceptor (FIG. 6). FAM-4-ROX, FAM-3-ROX and FAM-10-ROX were separated on a capillary and detected in red and green channels. For FAM-10-ROX the increased distance between the dyes reduces the amount of energy transfer, resulting in almost equal signals in the two channels. As the separation distance is reduced, the amount of energy transfer increases as evidenced by the reduced relative green signal. FAM-3-ROX and FAM-4-ROX both exhibit excellent energy transfer, but their mobilities are distinctly different, which offers the potential of tuning the mobility shift by varying the distance. To get an exact match of the mobility of two primers that have distinctly different emission spectra, FAM-3-FAM, FAM-4-FAM and FAM-10-FAM were also prepared. Among a library of primers prepared (FAM-N-FAM, FAM-N-TAM, FAM-N-ROX), it was found that sequencing fragments terminating in A, generated with FAM-10-FAM and FAM-3-ROX using Sequenase 2, have very similar mobility shifts (FIG. 7), demonstrating the potential for DNA sequence analysis. The emission of FAM-10-FAM and FAM-3-ROX are at 525 nm and 605 nm respectively.

B. Preparation of 12-mer Oligonucleotides Containing a Modified T and a FAM Label at the 5' Position.

The following three primers (SEQ ID NOs:37–39) were prepared on an ABI Model 394 DNA synthesizer in a 0.2 $\mu$mol scale:

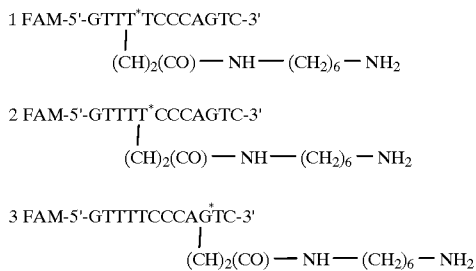

The modified base T* containing an amino linker arm was introduced to the defined position by using Amino-Modifier C6 dT phosphoramidite (Glen Research) and FAM was introduced by using 6-FAM amidite (ABI) in the last step of the synthesis. After the base sequences were completed, the oligonucleotides were cleaved from the solid support (CPG) with 1 ml concentrated $NH_4OH$. The amino protecting groups on the bases (A, G, C and T*) were removed by heating the $NH_4OH$ solution for 4 hours at 55° C. Capillary electrophoresis analysis indicated that the oligomers were ~80% pure, and they were used directly in the next dye-coupling step.

C. Attachment of the Second Fluorescent Dye to the Amino Linker Arm of the Oligomers 1, 2 and 3.

As a representative example, the reaction scheme to couple the second dye (TAM) to the oligomer 1 (SEQ ID NO:37) is shown below: The FAM-labeled oligonucleotides (1, 2 and 3) in 40 μL 0.5 M Na$_2$CO$_3$/NaHCO$_3$ buffer were incubated overnight at room temperature with approximately 150 fold excess of either TAM-NHS ester, ROX-NHS ester or FAM-NHS ester in 12 μL DMSO. Unreacted dye was removed by size exclusion chromatography on a Sephadex G-25 column. The two dye labeled oligonucleotides were then purified by 6 M urea-TBE, 20% acrylamide gel electrophoresis (40 cm×0.8 cm). The pure primers were recovered from the gel and desalted with Oligonucleotide Purification Cartridge (Applied Biosystems, Foster City, Calif.). The purity of the primers was shown to be >99% by capillary gel electrophoresis.

mobility of the primers. The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. As a representative example, FIG. 8 presents the absorption and emission spectra of the ET primer F10F, F10J, F3T and F3R. Each ET primer exhibits the characteristic absorption of FAM at 496 nm as well as strong absorption at 5.25 nm due to JOE in F10J, at 555 nm due to TAMRA in F3T and at 585 nm due to ROX in F3R. The fluorescence spectra of the ET

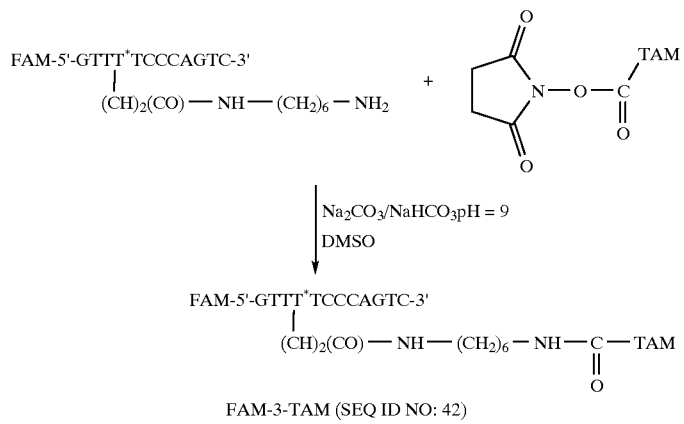

FAM-3-TAM (SEQ ID NO: 42)

D. Preparation of Additional Energy Transfer Labels

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 μl 0.5 M Na$_2$CO$_3$/NaHCO (pH 9.0) buffer were incubated overnight at room temperature with an approximately 150-fold excess of corresponding FAM, JOE, TAMRA and ROX N-hydroxysuccinimidyl esters in 12 μl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6 M urea (40 cm×0.8 cm). The purified primers were recovered from the gel slices and desalted with Oligonucleotide Purification Cartridge. The single dye-labeled primers with the same sequence as that of the ET primers were prepared by the standard protocol using Aminolink 2 (Applied Biosystems, Foster City, Calif.). The purity of the primers was shown to be >99% by polyacrylamide capillary gel electrophoresis. Primers were quantified by their 260 nm absorbances and then stored in 10 mM Tris-Cl, 1 mM EDTA (pH 8.0) at a final concentration of 0.4 pmol/μl for DNA sequencing reactions.

Figure 9:
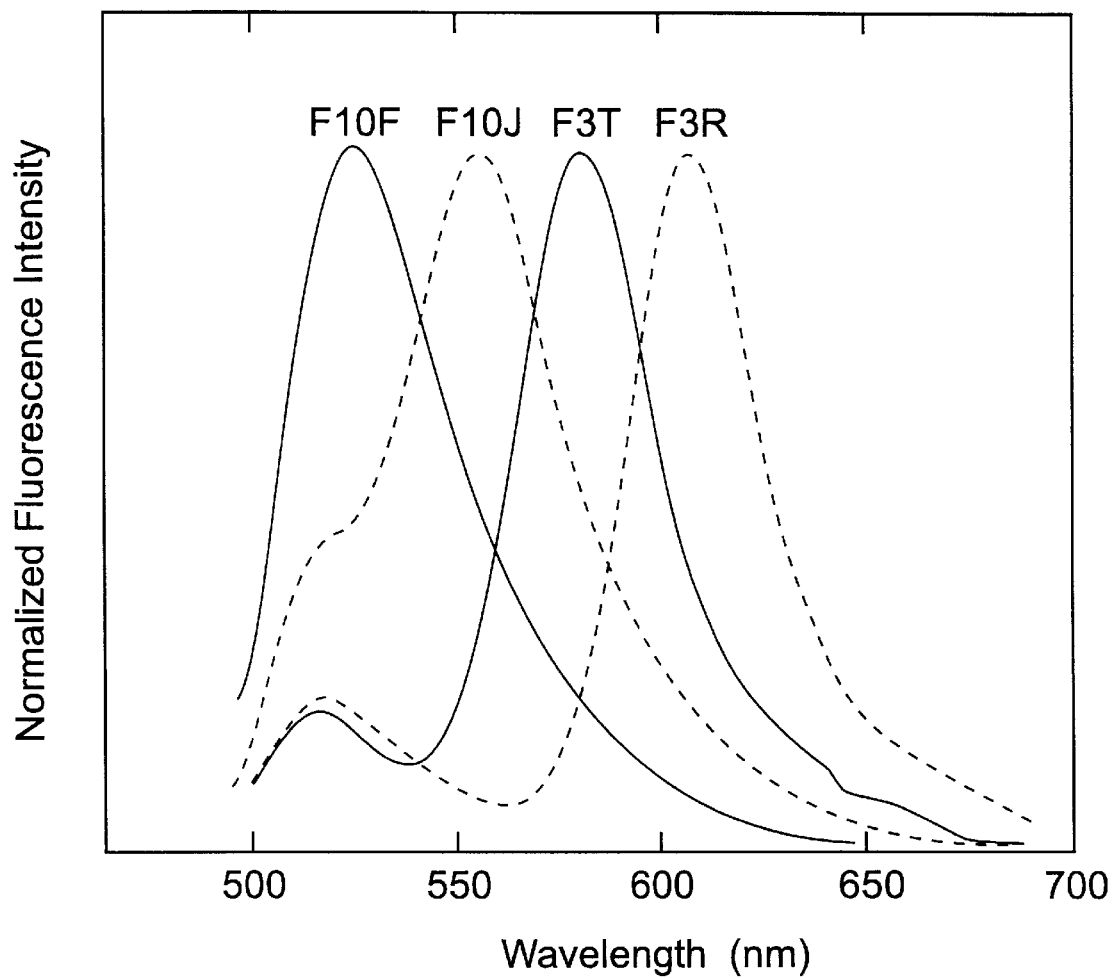
FIG. 9 shows the normalized fluorescence emission spectra of the four ET primers (F10F, F10J, F3T and F3R) (1×TBE, 7 M urea).
Figure 10C:
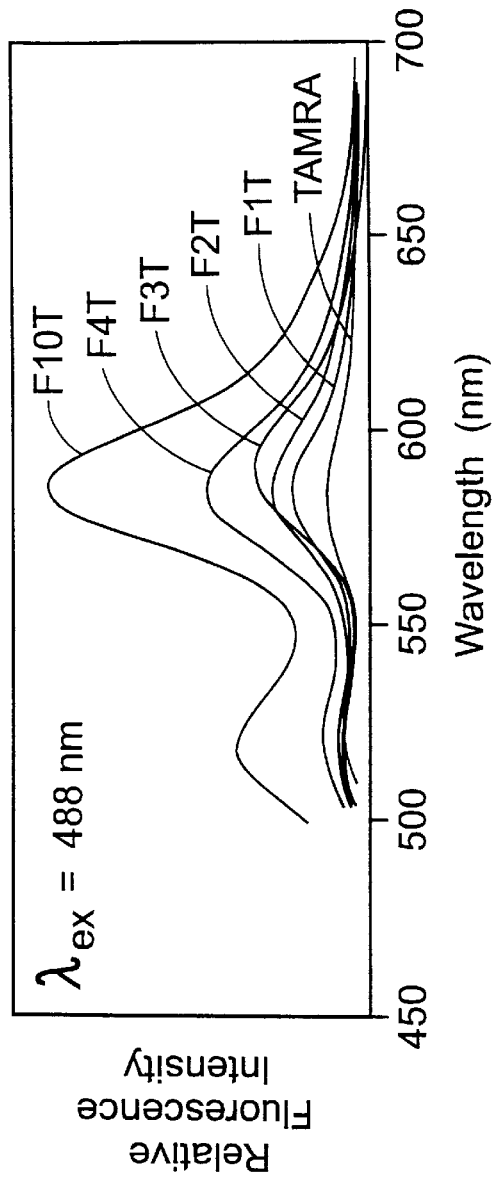
FIG. 10 shows that the fluorescence emission intensity of the ET primers is increased as the distance between the donor and acceptor increases. The emission spectra for each primer series were determined at the same molar concentration in 1×TBE.
Figure 10D:
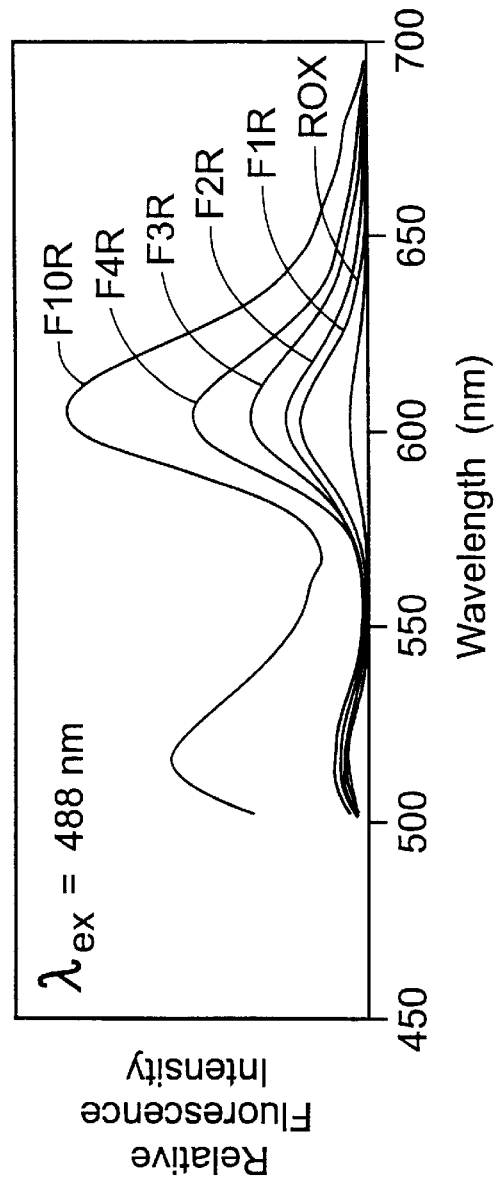
Figure 11:
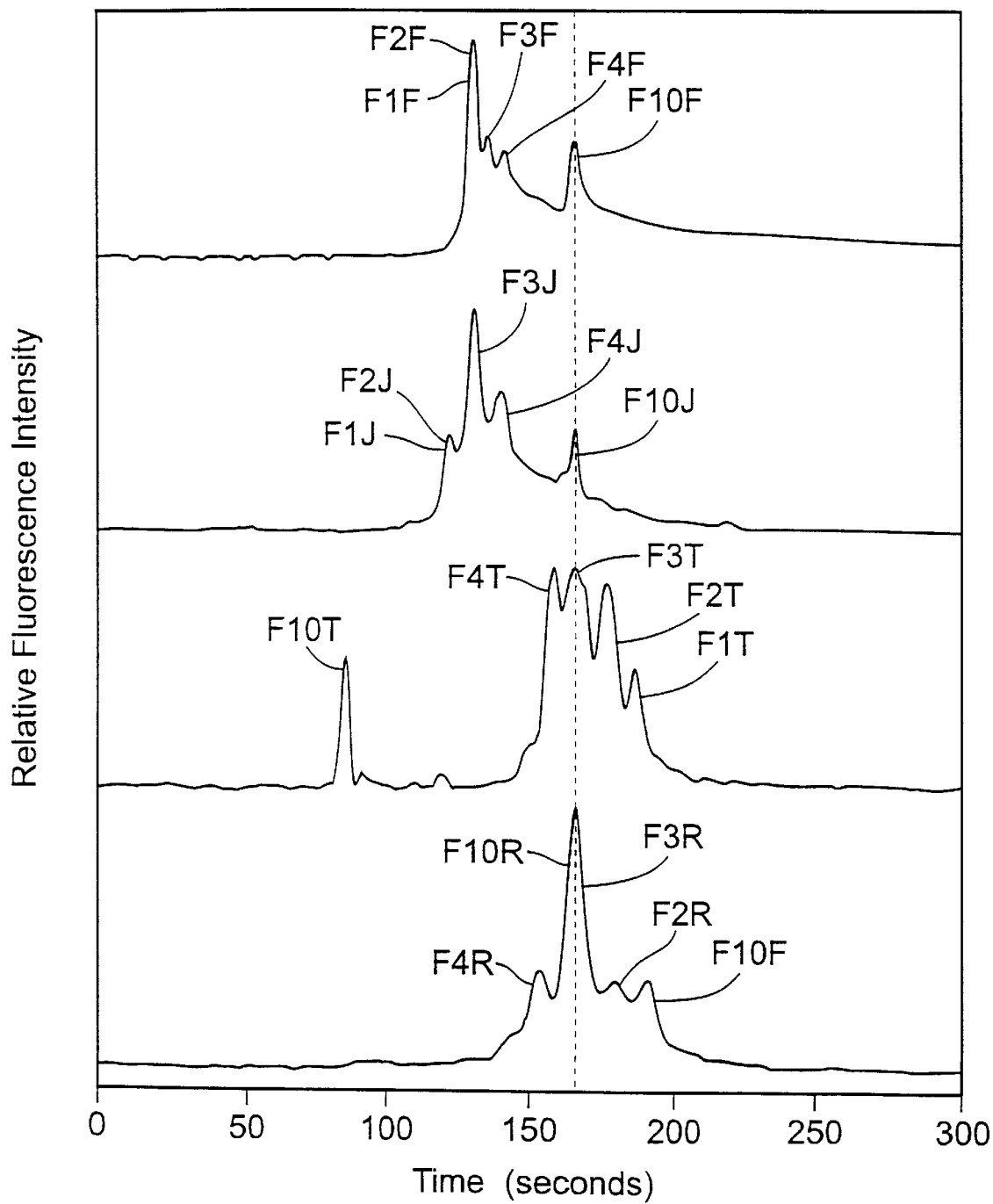
FIG. 11 shows capillary electropherograms of each ET primer series. A separate experiment has established that F10F, F10J, F3T and F3R have very similar mobilities. The mobilities of the other primers are shown for each set, relative to that of F10F, F10J, F3T and F3R, respectively. Sample was analyzed by typical capillary electrophoresis (CE) DNA sequencing conditions with 488 nm excitation.
Figure 12:
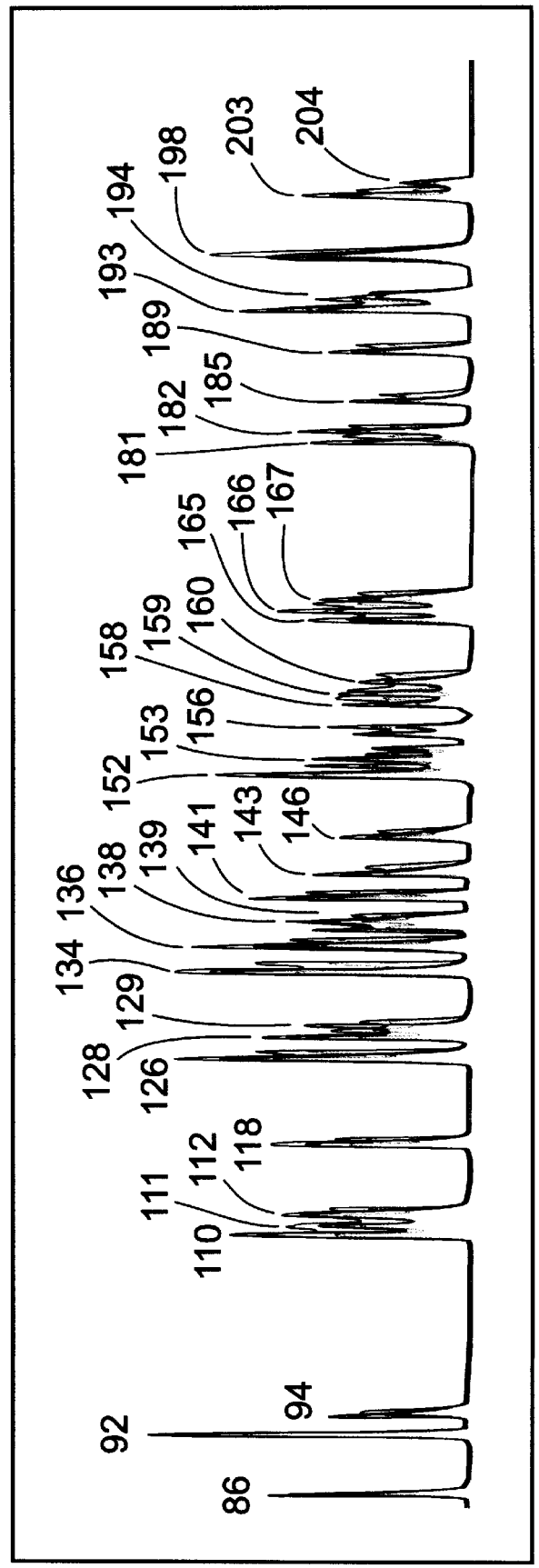
FIG. 12 shows that the mixed single base (ddATP/dNTPs) DNA sequencing fragments generated with F10F, F10J, F10T and F10R individually and then combined together have substantially the same mobility shift. Samples were prepared using Sequenase 2.0 Kit (USB/Amersham LIFE SCIENCE) and run on a 4-color CE DNA sequencer.

Twenty ET primers were synthesized with the same donor at 5' end and different acceptors at different positions on the primer sequence. The spacing between the two chromophores is altered by varying the position of T* in the synthesis of each primer. We found that the electrophoretic mobility of the ET primers depends on the spacing between the donor and acceptor. Within a range of distances determined by the number of intervening bases that allow good energy transfer, it is possible to adjust the electrophoretic primers are dominated by the acceptor emissions. While the emission maximum of F10F is at 525 nm, the emission of F10J with 488-nm excitation is Stokes-shifted to 555 nm, that of F3T is shifted to 580 nm, and that of F3R is shifted to 605 nm. In the case of F3R, the Stokes shift is over 100 nm. FIG. 8 also presents emission spectra of the single dye-labeled primers measured at the same molar concentration as that of the corresponding ET primers. Substantial enhancement of the ET primer emission intensity is observed compared to the corresponding single dye-labeled primers, indicating that efficient energy transfer is occurring. The fluorescence intensity improvements derived from FIG. 8 are: F10F=1.8×FAM; F10J=2.5×JOE or 1.4×JOE when JOE is excited at 514 nm; F3T=5.3×TAMRA or 1.7× TAMRA when TAMRA is excited at 514 nm; F3R=6.2× ROX or 2.3×ROX when ROX is excited at 514 nm. Thus, the fluorescence intensity of single JOE, TAMRA and ROX labeled primer with 514 nm excitation is still less than that of the corresponding ET primer with 488 nm excitation. To evaluate the emission spectral purity of the four ET primers, their normalized emission spectra are presented in FIG. 9. It can be seen that the residual emission of FAM in F10J, F3T and F3R is very small. Based on a comparison of the residual FAM emission in the ET primers with that of a FAM-labeled primer with same sequence and length, the energy transfer efficiency was calculated to be 65% for F10J, 96% for F3R and 97% for F3T. FIG. 10 presents the fluorescence intensity comparison of the ET primer series as well as the corresponding single dye-labeled primers measured at the same molar concentration. The results indicate that when the two fluorophores are too close to each other, fluorescence quenching occurs. The fluorescence intensity increases with the increase of the separation distances between the donor and acceptor. Strong fluorescence signals were obtained when the separation distance is 10-bases. The fluorescence intensity of F10T and F10R measured at the acceptor emission region is 10 and 14 times that of TAMRA and ROX primer respectively. Thus, the maximum fluorescence signals can be increased as much as 14-fold using the ET principle. The results also indicate that the donor FAM emission intensity in F10T and F10R is higher than the other ET primers. However, for a particular primer, as long as the acceptor emission is higher than or equal to that of the donor and the net fluorescence signal is intense, it is valuable for DNA analysis. The mobility comparison of ET primers on polyacrylamide capillary electrophoresis are shown in FIG. 11 which indicates that F10F, F10J, F10R, F3T and F3R have very similar mobility shifts. Although F10T has large mobility difference compared to F10F, F10J and F10R, FIG. 12 shows that the extended ddAPT/dNTPs DNA fragments generated with F10T have similar mobilities as those generated with F10F, F10J and F10R. This indicates that as the DNA fragments grow longer than 18 bases, DNA fragments generated with F10T have essentially the same conformation as fragments generated with F10F, F10J and F10R. For the successful application of donor-acceptor fluorophore labeled primers to DNA sequencing, it is useful that the primers produce same mobility shifts of the DNA fragments and display distinct fluorescence signals. Six primers (F10F, F10J, F10T, F10R, F3T and F3R) were therefore selected for evaluation in DNA sequencing.

II. Preparation of STR Samples for Denaturing Gel Analysis

ET primers for PCR were synthesized by the phosphoramidite method on an Applied Biosystems 392 DNA synthesizer. The structures of the blank and energy-transfer dye-labeled PCR primers for VWFA, THO1, TPO, and CSF loci are presented in Scheme III. Primer sequences followed published sequences (THO1 (Edwards et al., Am. J. Hum. Genet. (1991) 49:746–756), TPO (Huang et al., Forensic Science International (1995) 71: 131–136; CSF (Hammond et al., Am. J. Hum. Genet. (1994) 55: 190–195), VWFA-B (Kimpton et al., PCR Methods and Applications (1993) 3:13–22) except VWFA-B which was redesigned to avoid hairpins and dimer formation; as a result, VWFA products are 5 bp longer than those reported by Kimpton (1993). The energy-transfer dye-labeled primers are advantageous for two-color fragment sizing because the 488-nm exciting light is optimally absorbed by the FAM chromophore in these primers followed by enhanced emission at the FAM wavelength for the THO1 locus (amplified with F6F) and for the VWFA, TPO and CSF loci (amplified with F8F primers), or very distinctively Stokes-shifted emission following energy transfer in the case of the M13 A-termination ladder (generated with the F10R primer (Wang et al., Anal. Chem. (1995) 67:1197–1203 and Ju et al., Anal. Biochem. (1995) 231: 131–140). Primers were dissolved in 10 mM Tris-HCl, 1 mM EDTA buffer at a final concentration of 10 $\mu$M for PCR reactions and 0.4 $\mu$M for the M13 sequencing reaction.

For PCR amplification of multiplexed STR loci, DNA was isolated from blood using standard methods (Sambrook, J., Fritsch, E. F., Maniatis, T., Molecular Cloning: A Laboratory Manual, (2nd ed. Cold Spring Harbor Laboratory, Cold Spring Harbor, N.Y.)(1989)). PCR multiplex amplifications for VWFA, THO1, TPO, and CSF loci were performed in 25 $\mu$l volumes using 10 ng genomic DNA template, 0.5 $\mu$M of each forward fluorescent and reverse blank primers for VWFA, THO1 TPO and CSF loci, 2.5 units of Taq DNA polymerase, 50 mM KCL, 1.5 mM MgCl$_2$, 10 mM Tris-HCL at pH 8.3 and 200 $\mu$M dNTPs (final concentrations indicated). The PCR cycle protocol using a Perkin Elmer Cetus Model 480 was: (1) melting at 95° C. for 3 min, (2) 28 cycles at 95 ° C. for 1 min. then 59° C. for 1 min, then 72° C. for 2 min to complete extension.

The locus types for all samples used in this study were independently determined by analysis on slab gels essentially as described by Puers et al., Am. J. Hum. Genet. (1993) 53:953–958, with SybrGreen staining and detection on a Molecular Dynamics FluorImager 575.

III. Sequencing Applications with Energy Transfer Primers

Figure 13:
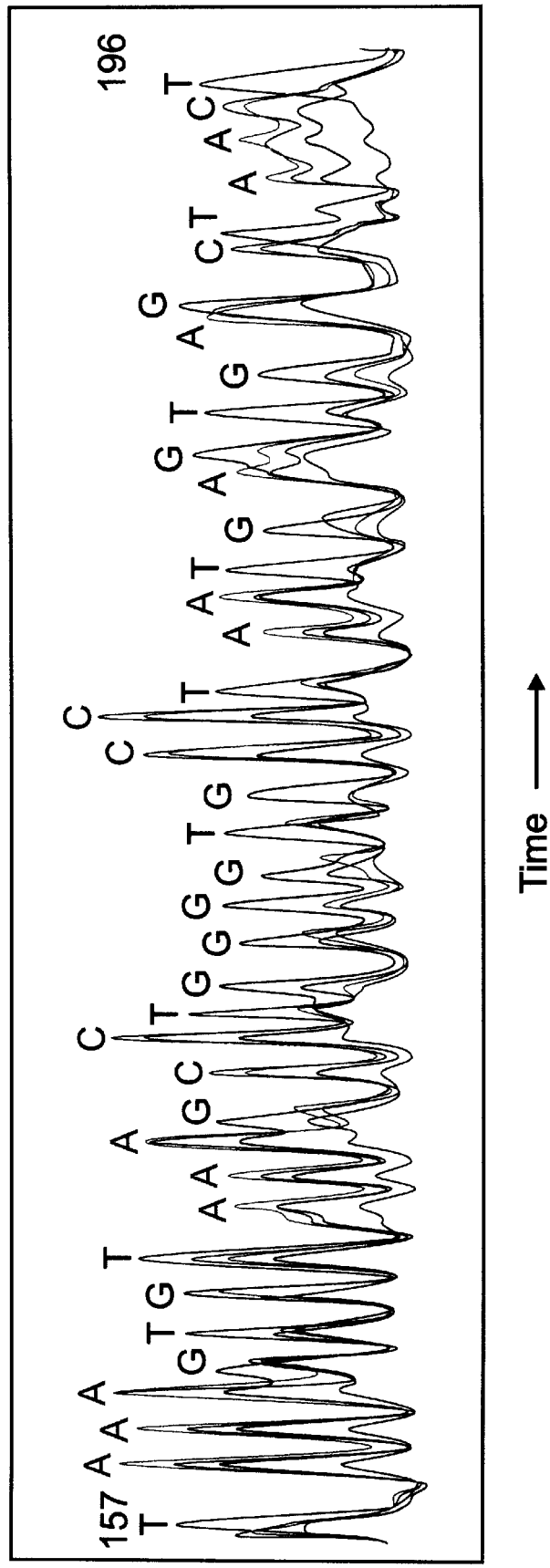
FIG. 13 shows a portion of 4-color raw data (base 157 to 19) of DNA sequencing profile of M13mp 18 DNA using the ET primer F10F, F10J, F10T and F10R and Sequenase 2.0. Primer concentration: 0.4 pmol; DNA template: 0.8 µg (0.2 µg for each base extension).

DNA sequencing using primers F10F, F10J, F10T and F10R on CE sequencer was performed using 0.4 pmol of primer and 0.2 $\mu$g of template DNA for each base extension. The sequences extended to more than 600 bases, a portion of which (raw data) is shown in FIG. 13. From this raw data, sequences can be determined by the color on the top peak of the electropherograms. This is the first 4-color sequencing plot without any mobility shift adjustment.

ET primers described here also provide better results and higher sensitivity on the commercial 4-color DNA sequencer. To demonstrate the advantage of ET primers versus conventional single-dye labeled printers. DNA sequencing samples generated with primer F10F, F3T and F3R were analyzed on an Applied Biosystems 373A sequencer. Single base extension (ddTTP/dNTPs) experiments were performed to examine the relative mobility shift and sensitivity of DNA fragments generated with the ET primers. FIG. 14 presents raw fluorescence intensity traces from electrophoresis run on an ABI 373A sequencer. The graphs in FIG. 14A were obtained using M13 (–40) primers labeled with single dye molecules. The differences in electrophoretic mobility of the DNA fragments can be clearly seen. The TAMRA- and ROX-labeled fragments migrate about one base slower than the FAM- and JOE-tagged DNA fragments and have dramatically weaker fluorescence intensities. The corresponding runs with the ET primers are presented in FIG. 14B. The mobilities of the DNA fragments are more closely matched (less than a quarter of a base difference).

To further quantify the instrument sensitivity with the ET primers under slab gel conditions, reactions were run using a constant amount of primer (0.4 pmol) and varying the amount of M13mp18 template DNA (0.05–1 pmol). Graphs of several band intensities against quantity of template were made. This method indicates that the sensitivity for the F10F primer is 160% that of the FAM primer. Similarly, the sensitivity for the F10J, F3T and F3R primers is 360%, 400% and 470% that of JOE, TAMRA and ROX primers, respectively. In experiments which included an excess of template DNA over primer, only a small fraction of either ET or single-dye labeled primer remained unextended. Thus, no significant difference was seen in the efficiency with which the ET primers were extended by polymerase compared with single-dye labeled primers.

Typical raw fluorescence intensity traces for 4-dye, single lane sequences are presented in FIGS. 14C and 14D. Shown here is a portion from the middle of the run spanning about 45 bases. On this intensity scale, the peaks from the red filter are barely discernible when single ROX-labeled primer is used (C). In contrast, all of the sequence-dependent intensity fluctuations are readily seen with the ET primers in the raw data (D). While four-color sequences run with this instrument typically require 3-fold more template and 2-fold more primer in the reactions containing TAMRA- and ROX-labeled primers, the four reactions use(d for FIG. 14D contained equal amounts of ET primer and template. This change in reaction balance was made possible by the increased relative intensities of the F3T and F3R primers. With these four primers, DNA sequencing on M13Mp18 template produces 510 bases with accuracy of over 99.8%. This sequence can be obtained using a total of 0.6 $\mu$g (0.24 pmol) of M13 template DNA which is approximately one-fourth the amount of template DNA required to give similar sequence accuracy with single dye-labeled primers.

IV. Polymerase Chain Reaction Applications Employing ET Primers

A. Rapid Sizing of Short Tandem Repeat (STR) Alleles Using Energy-Transfer (ET) Fluorescent Primers and Capillary Array Electrophoresis 1. Instrumentation.

Capillary array electrophoresis separations were detected with the laser-excited, confocal-fluorescence scanner as previously described by Huang et al.(Huang et al. (1992) Anal. Chem. 1992, 64, 967–972. and Anal. Chem. 1992, 64, 2149–2154). Briefly, excitation light at 488 nm from an argon ion laser is reflected by a long-pass dichroic beam splitter, passed through a 32×, N.A. 0.4 microscope objective, and brought to a 10 μm diameter focus within the 75 μm i.d. capillaries in the capillary array. The fluorescence is collected by the objective, passed back through the first beam splitter to a second dichroic beam splitter that separates the red (λ>565 nm) and green (λ<565 nm) detection channels. The emission is then focused on 400 μm diameter confocal pinholes, spectrally filtered by a 590 nm long-pass filter (red channel) or a 20 nm band-pass filter centered at 520 nm (green channel), followed by photomultiplier detection. The output is preamplified, filtered, digitized, and then stored in an IBM PS/2 computer. A compter-controlled stage is used to translate the capillary array past the optical system at 20 mm/s. The fluorescence is sampled unidirectionally at 1500 Hz/channel. The scanner construction and operation have recently been described in detail (Mathies et al. (1994), Rev. Sci. Instrum. 65, 807–812). Postacquisition image processing was performed with the programs IPLab, KaleidaGraph and Canvas.

2. Capillary Electrophoresis.

Polyacrylimide-coated, fused-silica capillaries were prepared using a modification of the procedure described by Hjerten et al. ((1985), J. Chromatogr. 347, 191–198). A 2–3 mm wide detection window was produced by burning off the polyimide coating with a hot wire followed by cleaning the external surface with ethanol. The detection window was placed 25 cm from the injection ends of the 75 μm i.d., 350 μm o.d., 50 cm long fused silica capillaries (Polymicro Technologies, Phoenix, Ariz.). The inner walls of the capillaries were incubated with 1 N NaOH for 30 min at room temperature, followed by rinsing with deionized water. The capillaries were then treated Overnight at room temperature with γ-methacryloxypropyl-trimethoxysilane (1:250 dilution with $H_2O$ adjusted to pH 3.5 with acetic acid) to derivatize the walls for acrylamide binding. Freshly-made 4% T acrylamide solution in ½×TBE buffer (45 nM tris, 45 mM boric acid, 1 mM EDTA, pH 8.3) was filtered with a 0.2 μm syringe filter and degassed under vacuum for 30 min. One μl TEMED (tetramethylethylenediamine) and 10 μl of 10% APS (ammonium persulfate) solution were added to 1 ml of gel solution. The solution was immediately forced into the capillary with a 100-μl syringe. After 30 min, the acrylamide solution was flushed out with deionized water and capillaries were filled with buffer consisting of hydroxyethyl cellulose (HEC) ($M_n$=438,000, Aqualon Co. Hopewell, Va.) dissolved in ½×TBE. The separation buffer was prepared by adding 0.8 g HEC to 100 ml ½×TBE and dissolved by stirring overnight at room temperature. The HEC buffer was degassed under vacuum for 30 min, centrifuged for 20 min on a tabletop centrifuge, drawn into a 100-μl syringe, and 3 μl sample was used for injection into each capillary. Capillaries were prerun at 80 V/cm for 5 min before each experiment. Diluted and deionized PCR samples were injected by inserting the capillary in a 5-μl sample volume held in an Eppendorf tube followed by electrokinetic injection (80 V/cm for 3 s). After injection, the sample tubes were replaced with tubes containing 0.8% HEC plus ½×TBE buffer. Electrophoresis was performed at 80 V/cm using 5-capillary arrays held at ambient temperature (22° C.). The low (80 V/cm) electrophoresis voltage was used to avoid undersampling of the bands with our current detection system which is limited to 1 Hz scan rates. When the experiments were complete, capillaries were flushed with water, then with methanol followed by drying. These coated capillaries could be refilled 20–25 times before the quality of the separations deteriorated. Methods for the further extension of the lifetime of capillary columns have been described.

3. PCR Amplification of THO1 loci.

DNA was isolated from blood by using standard methods (Puers et al. (1993) Am. J. Hum. Genet. 53, 953–958). The human tyrosine hydroxylase locus HUMTHO1, chromosomal location 11p15.5, contains a polymorphic four base STR sequence (AATG) in intron 1[Puers, 1993, 953]. PCR-amplification of this polymorphic region produces allelic fragments designated "5" through "11", according to the number of AATG repeats; an additional allele designated "9.3" differs from allele 10 by a single base deletion. The primer sequences used for PCR are 5'-ATTCAAAGGGTATCTGGGCTCTGG-3' (THO1-A) (SEQ ID NO:31) and 5'-GTGGGCTGAAAAGCTCCCGATTAT-3' (THO1-B) (SEQ ID NO:40) (Edwards et al. (1991) Am. J. Hum. Genet. 49, 746–756). PCR amplifications were performed in 50 μl volumes by using 10 ng genomic DNA template, 0.5 μM of each primer, 5 units Taq DNA polymerase, 50 mM KCl, 1.5 mM $MgCl_2$, 10 mM Tris-HCl at pH 8.3, and 200 μM dNTPs (final concentrations indicated). The PCR cycle protocol using a Perkin Elmer Cetus Model 480 was: (1) melting at 95° C. for 5 min, (2) 30 cycles of 95° C. for 1 min 58° C. for 1 min, and 72° C. for 1 min, (3) 72° C. for 7 min to complete extension. The PCR sample was then dialyzed for 30 min by pipeting 8–10 μl onto a 0.10 μm VCWP membrane filter (Millipore, Bedford, Mass.) wvhich was floated on deionized water in a beaker held at 4° C. Dialysis was used to remove salts which can interfere with sample injection. Following dialysis, the samples were diluted with deionized water 100–1000 times (depending on product concentration) before electrokinetic injection. The amplifications with fluorescently labeled primers were also performed as described above. Initially four sets of fluorescent primers were used for PCR amplification and the mobility shifts of the products were evaluated with capillary electrophoresis. For these mobility shift experiments, 1–2 ng of inlabeled PCR product was reamplified by 20 PCR cycles using the appropriate fluorescent primers. THO1 types for all samples used in this study were independently determined by analysis on slab gels essentially as described by Puers et al., supra. Standard reference alleles were determined by sequence analysis.

4. Design and Synthesis of ET Primers.

Chemicals were purchased from Applied Biosystems (Foster City, Calif.). Oligodeoxynucleotides were synthesized by the phosphoramidite method on an Applied Biosystems 392 DNA synthesizer. Absorption spectra of the primers were measured on a Perkin-Elmer Lambda 6 UV-visible spectrophotometer and fluorescence emission spectra were taken on a Perkin-Elmer model MPF 44B spectrofluorimeter.

Figure 15:
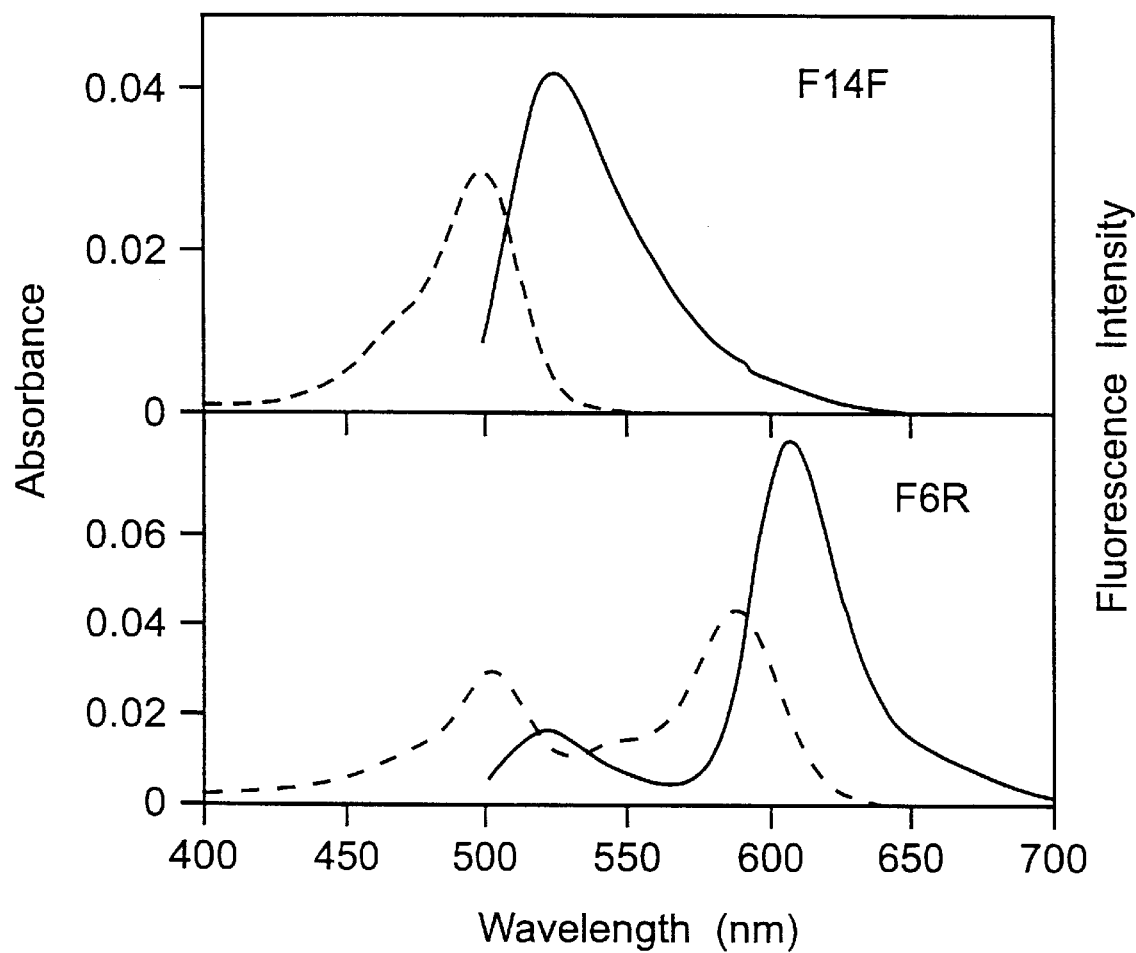
FIG. 15 shows the absorption (----) and fluorescence emission (——) spectra of the fluorescently labeled THO1 primers F14F and F6R measured in 1×TBE. F14F exhibits strong absorption at 488 nm and intense fluorescence emission with a maximum at 525 nm. F6R also exhibits intense absorption at 488 nm but the maximum emission is shifted out to 600 nm.

The structures of the four ET primers and a representative synthetic reaction are presented in Scheme 2. The THO1 primer (24-bases long) with the sequence 5'-ATTCAAAGGGTATCTGGGCTCTGG -3' (THO1-A) (SEQ ID NO:31) and 5'-GTGGGCTGAAAAGCTCCCGATTAT-3' (THO1-B) (SEQ ID NO:40) were synthesized with donor-acceptor fluorophore pairs separated by different distances in the manner described above, where each of the 24-mers contains a modified base (T*) with the donor dye being attached to the 5' end of the oligomer, and the acceptor dye being attached to the primary amine group on the modified base (T*). As a representative example, the structure of F6R is shown below)w (Structure 3).

acceptors at different positions on the primer sequence. The energy-transfer dye-labeled primers are advantageous for two-color fragment sizing because the 488-nm exciting light is optimally absorbed by the FAM chromophore in these primers followed by enhanced emission at the FAM wavelength in the case of F10F and F14F or very distinctively Stokes shifted emission following energy transfer in the case of F2R and F6R. As representative examples, spectra of F14F and the energy transfer dye-labeled primer F6R are presented in FIG. 15. F14F exhibits strong absorption at ~488 nm and intense fluorescence emission with a maximum at 525 nm. F6R also exhibits intense absorption at 488 nm, but because of the FAM-to-ROX fluorescence energy transfer, the emission maximum is shifted out to ~600 nm

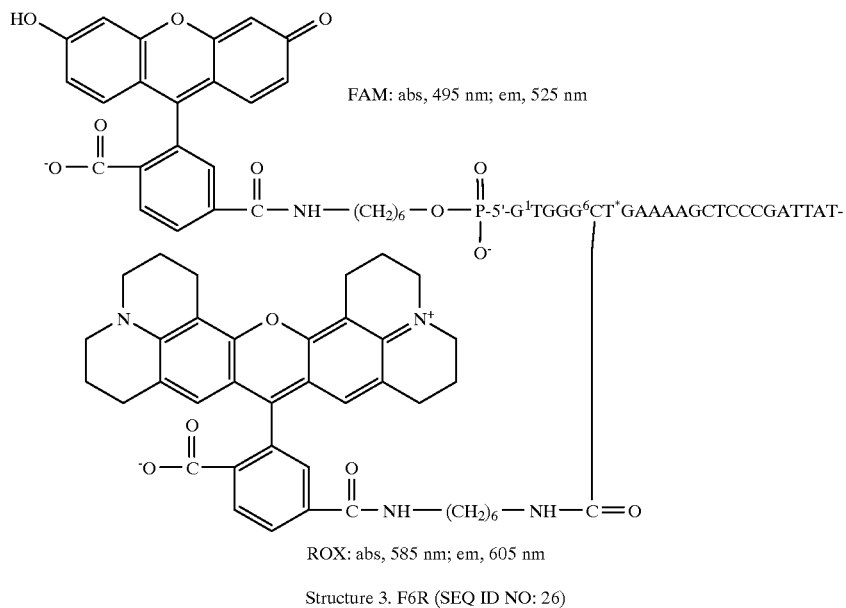

Structure 3. F6R (SEQ ID NO: 26)

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 μl 0.5 M $Na_2CO_3$/$NaHCO_3$ (pH 9.0) buffer were incubated overnight at room temperature with an approximately 150-fold excess of corresponding ROX or FAM N-hydroxy succinimidyl esters in 12 μl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6 M urea (40 cm×0.8 cm). The purified primers were recovered from the gel slices and desalted with Oligonucleotide Purification Cartridge (ABI). The single dye-labeled primers with the same sequence as that of the ET primers were prepared by the standard protocol using Aminolink 2 (ABI). The purity of the primers was shown to be >99% by polyacrylamide capillary gel electrophoresis. Primers were quantified by their 260 nm absorbances and then stored in 10 mM Tris-HCl, 1 mM EDTA (pH 8.0) at a final concentration of 10 pmol/μl for PCR reactions.

Figure 16:
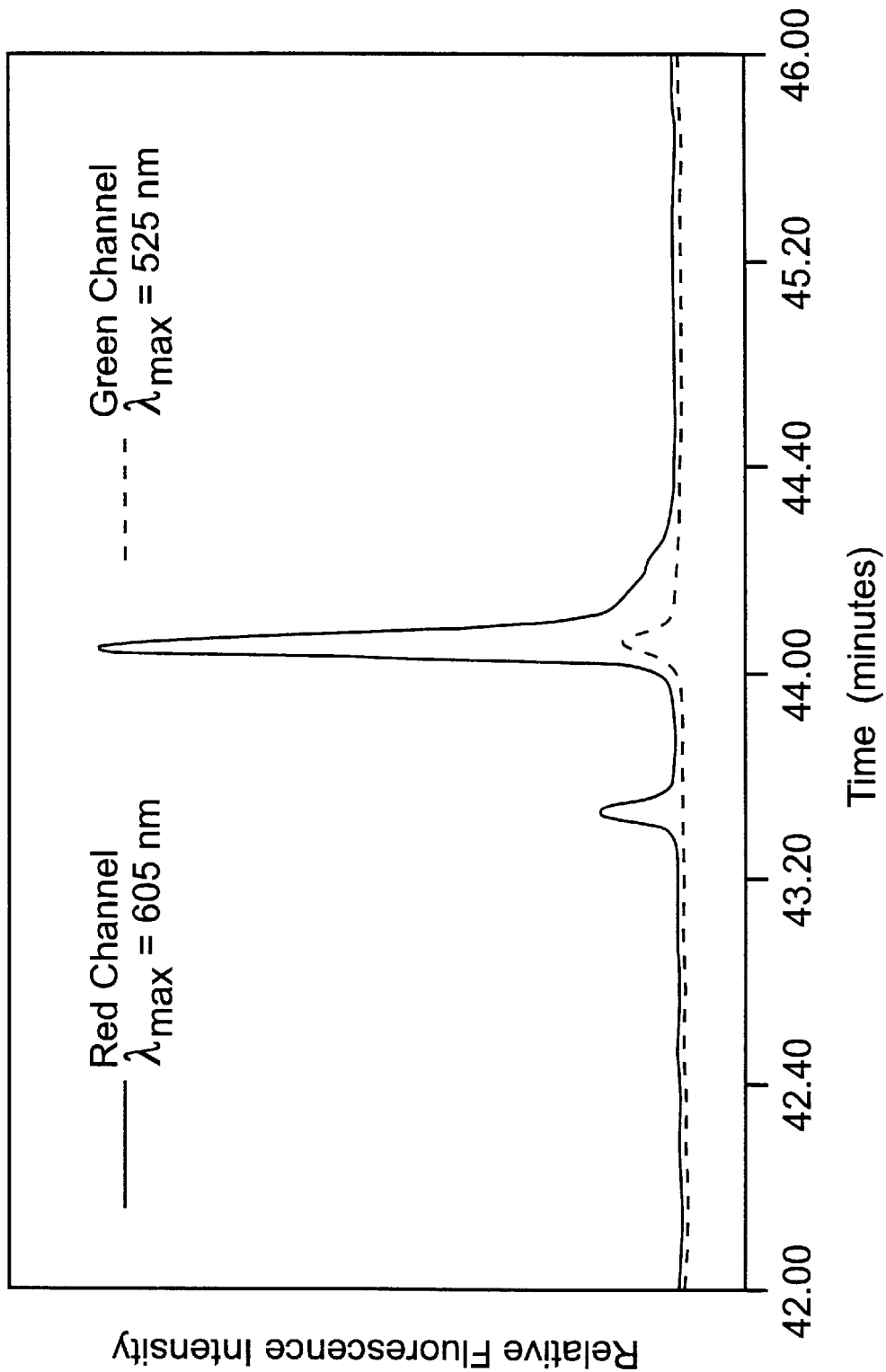
FIG. 16 shows the capillary electrophoresis (CE) electropherogram of primer F6R and ROX labeled primer. The two primers with the same sequence and same molar concentration were mixed together in 80% formamide and analyzed with a polyacrylamide gel filled capillary. The fluorescence signals were detected in the green (----) and red (——) channels simultaneously with 488 nm excitation (argon laser). The fluorescence signal intensity of F6R is 8-fold higher than that of ROX labeled primer.

Four ET primers (F2R, F6R, F10F and F14F) were synthesized with the same donor at 5' end and different and the energy transfer efficiency is over 90%. Substantial enhancement of the ET primer emission intensity compared to the single dye-labeled primer is observed. For example, FIG. 16 shows the fluorescence signal intensity comparison of the ET primer F6R with the corresponding single ROX-labeled primer in capillary electrophoresis. The two primers with the same sequence and same molar concentration were mixed together in 80% formamide and analyzed with a polyacrylamide gel filled capillary. The fluorescence intensity of F6R primer is 8-fold higher than and the ROX primer.

5. Evaluation of Energy Transfer Primer Labeling.

For routine sizing experiments it is desirable to perform 2-color detection where the allelic standards are amplified with one fluorescent primer and the unknowns are amplified with a second fluorescent primer having a distinctive emission. Energy-transfer (ET) primers have the advantage of providing strong absorption at a common laser excitation wavelength (488 nm). Following the fluorescence energy transfer, the ET primers emit at a Stokes-shifted wavelength determined by the properties of the acceptor. Thus, the fluorescence emission of the ET primers is very intense, and the emission spectra of the different ET dye-labeled primers are compared to conventional single-dye labeled fluorescent primers as shown earlier. Furthermore, the mobility shift of DNA fragments generated with ET primers depends on the spacing between the dyes. Experiments were therefore performed to evaluate the mobility shift of the amplified fragments for all combinations of singly and doubly labeled targets.

Figure 17:
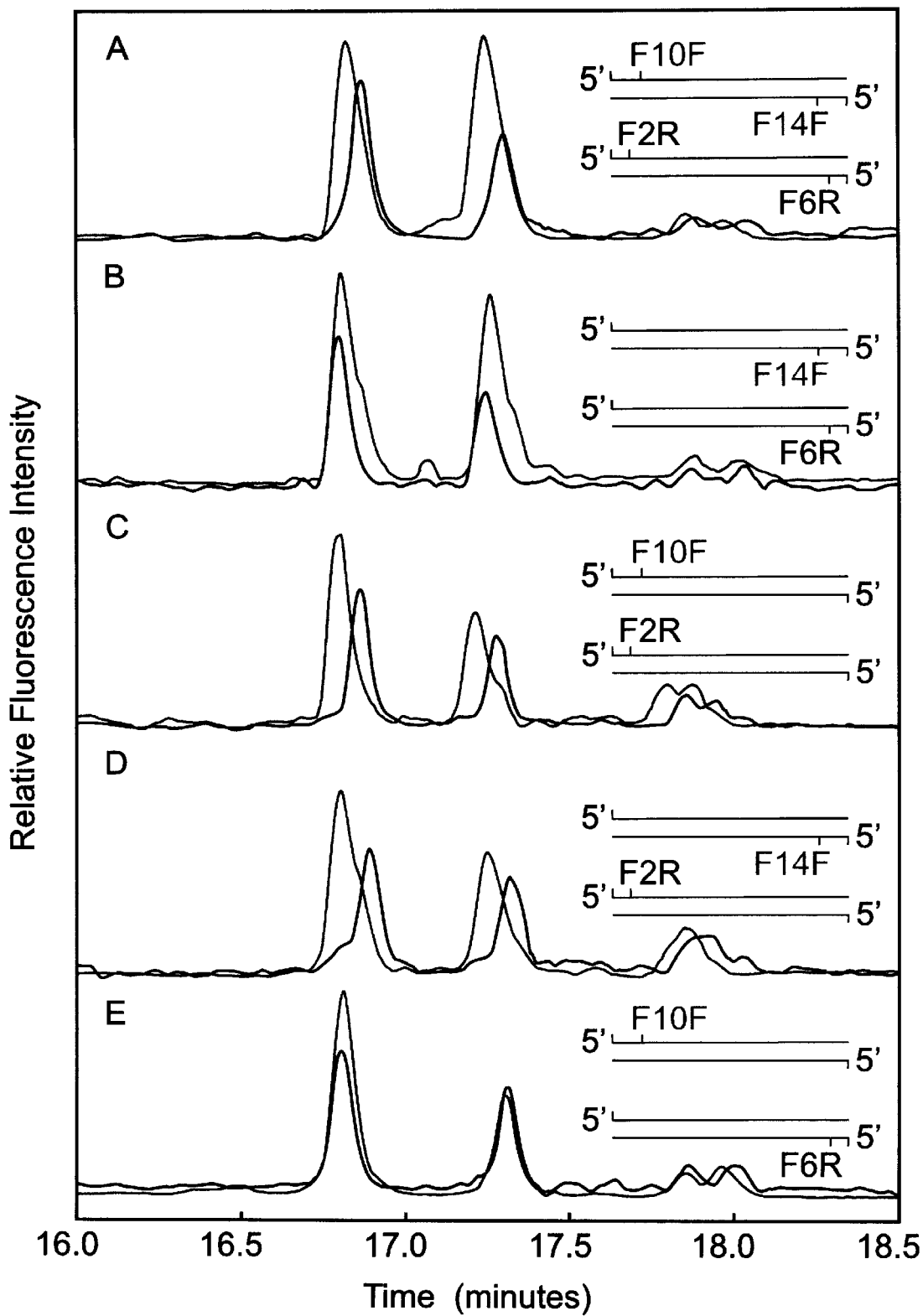
FIG. 17 shows the comparison of the mobility shift using five different ET primer-dependent methods for the amplification of the THO1 target alleles 6 and 9.3. The green line indicates the fluorescence intensity in the green channel and the red line indicates the intensity in the red channel. The structures of the primer sets used are indicated. Electrophoresis was performed using 0.8% HEC, ½×TBE and 1 µM 9-aminoacridine (9-AA) in the running buffer.

In trace A of FIG. 17, both strands (if the amplified 6 and 9.3 targets have been labeled. In one case, the F10F primer is extended to form the (+) strand and the F14F primer is extended to form the (–) strand producing the green-emitting fragments. In the second case, the ET dye-labeled primer F2R is extended to produce the (+) strand and F6R is used to extend the (–) strand producing the red-emitting fragments. These fragments were mixed and electrophoresed on HEC-filled capillaries in the presence of 1 μM 9-aminoacridine (see below). The motility shift between the green fragments and the red fragments in trace A was found to be ~2 bp. Thus, it was decided to evaluate amplifying with just one fluorescent primer per ds-DNA fragment to see if a particular combination of labels would reduce the mobility shift. Trace B in FIG. 17 shows that amplifying the (–) strand with the F14F primer or with the F6R primer generates fragments having almost no mobility shirt (≦0.3 bp) between the green- and the red-labeled fragments. The two other labeling methods shown in traces C and D resulted in larger mobility shifts (2.4 bp). However, amplifying the (–) strand with F6R and the (+) strand with F10F also produced fragments having almost no mobility shift (trace E). The subsequent experiments A ere performed using the labeling method illustrated in trace B because these fragments are labeled on the same strand and can thus also be sized under denaturing conditions if necessary.

6. Resolution Enhancement with 9-Aminoacridine.

To achieve satisfactory resolution of the THO1 allelic ladder, it was found that it is necessary to include an intercalating dye, in the running buffer. Poorer resolution is obtained when the allelic ladder (amplified with the F6R primer) is run in 0.8% HEC alone. The separation of the same ladder in 0.8% HEC plus 1 μM of the intercalating dye thiazole orange (TO) provided dramatically enhanced resolution. Electrophoresis in the presence of the intercalator ethidium bromide has also been shown to improve the electrophoretic resolution of ds-DNA.(Schwartz et al. (1991) J. Chromatogr. 559, 267–283; Guttman et al. (1991) Anal. Chem. 63, 2038–2042). Unfortunately, TO contributes to the signal in the green channel of our two-color detection system rendering it unsuitable for use in the desired two-color labeling scheme. It is thus necessary to use a non-fluorescent intercalator to improve the resolution. In electrophoretic separations of preformed dimeric dye: DNA complexes, Zhu et al.((1994) Anal. Chem. 66, 1941–1948) observed that the addition of the non-fluorescent dye 9-aminoacridine (9-AA) can be used to dramatically improve ds-DNA separation much like TO and ethidium. Thus, the effect of 9-AA was evaluated. The separation is as good as hat obtained in the presence or TO. The resolution improves significantly up to 1 μM 9-AA and is only slightly better at 5 μM. 9-AA concentrations above 50 μM were found to quench the fluorescence.

7. Two-color THO1 Sizing with Capillary Array Electrophoresis.

Figure 18:
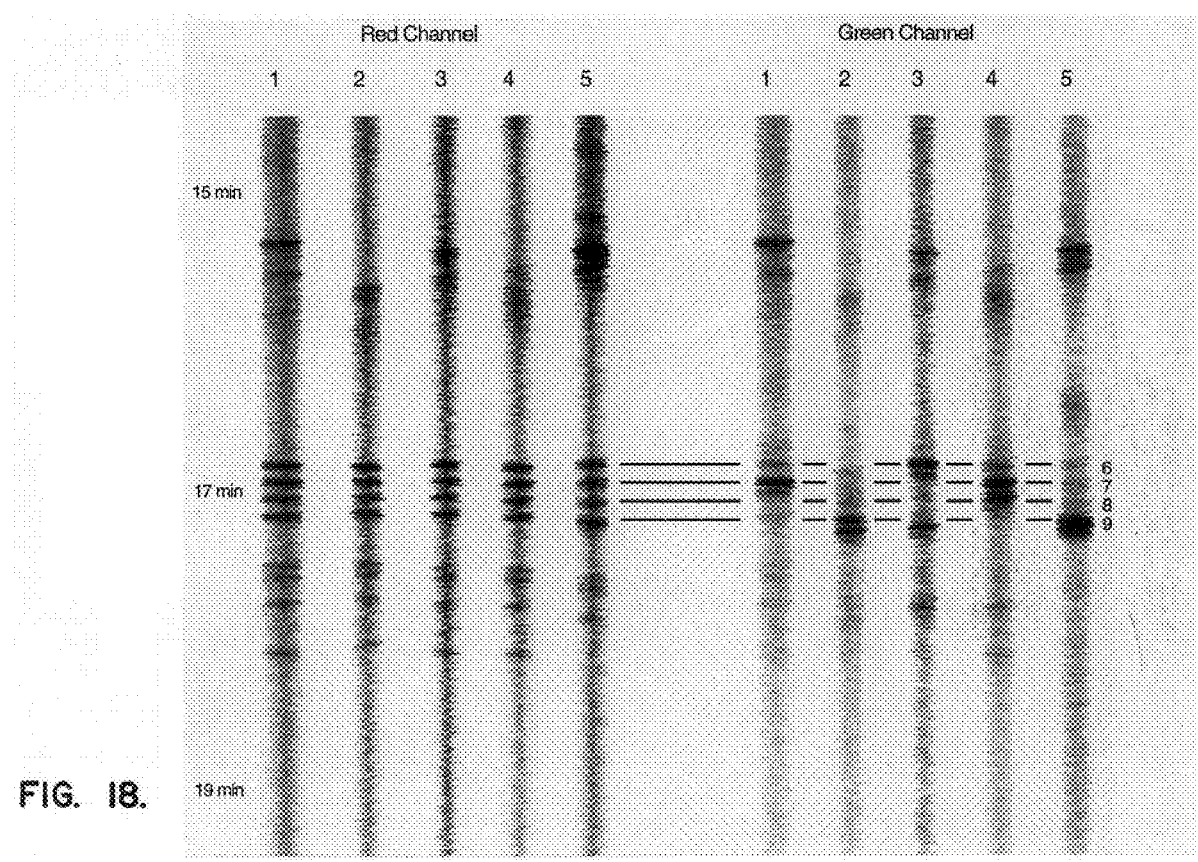
FIG. 18 shows the images of the fluorescence from a five capillary array separation of THO1 alleles. The left image presents the fluorescence signal as a function of time detected in the red (>590 nm) channel while the right image presents the fluorescence signal from the green ($\lambda$max=525 nm) channel. The standard THO1 allelic ladder (6+7+8+9) was amplified with the red emitting ET primer F6R and detected in the red channel; unknown alleles were amplified with the green emitting primer F14F and detected in the green channel. These images have been adjusted for the 1–2% capillary-to-capillary variance in mobility by shifting the time axes so that the allelic ladder is detected at the same time in all capillaries. This separation was performed with 0.8% HEC and 1 µM 9-AA in the running buffer at 80 V/cm.
Figure 19:
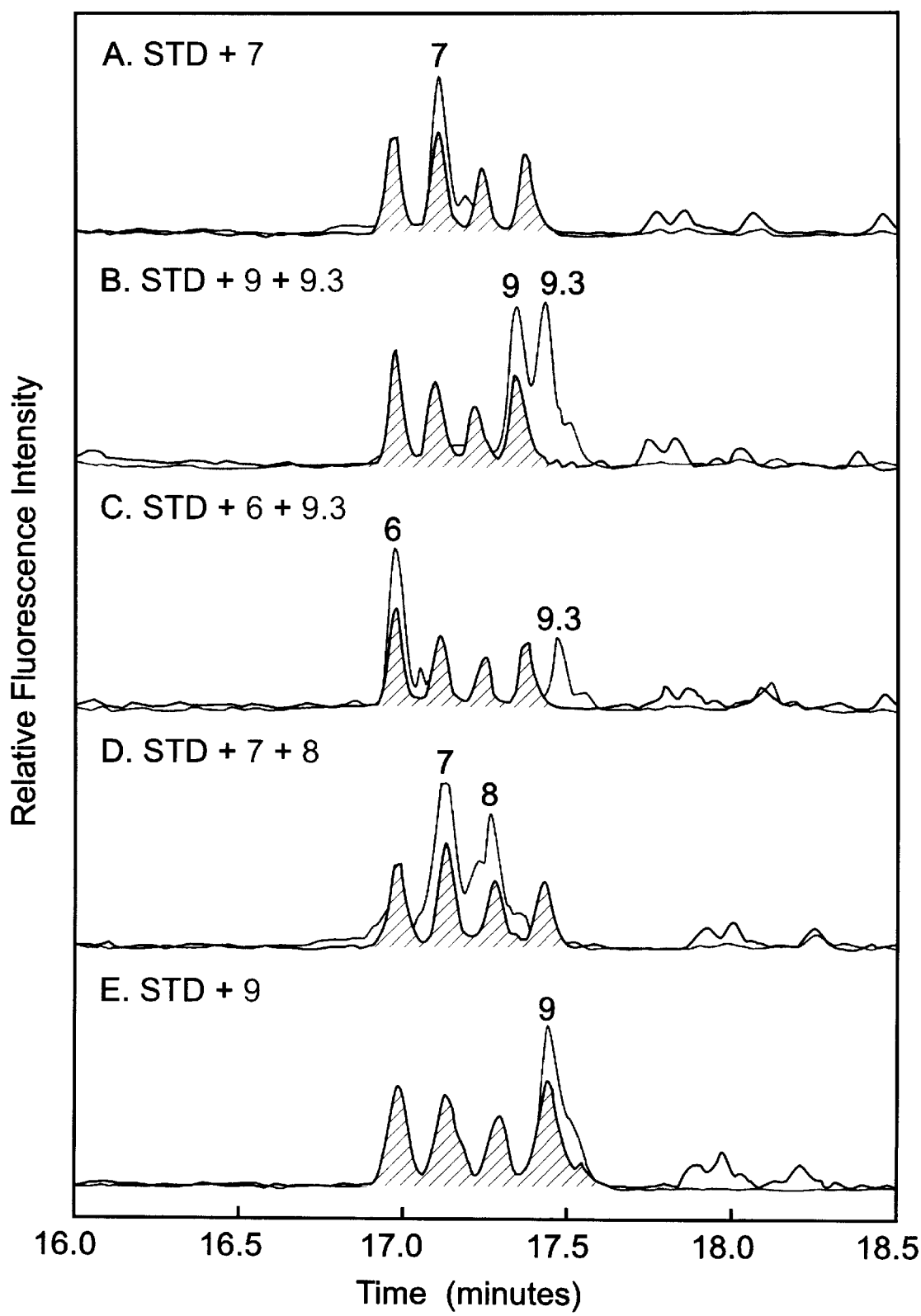
FIG. 19 shows the electropherograms of the THO1 fragment sizing separations presented in FIG. 18. The green signal is from the unknown alleles and the red signal is from the standard THO1 ladder. Traces A through E correspond to lanes 1–5 in FIG. 18.

FIG. 19 presents the results of a typical THO1 sizing experiment performed using two-color capillary array electrophoresis. The standard allelic ladder was amplified with F6R and detected in the red channel, while the unknown alleles were amplified with F14F and detected in the green channel. The signal detected as a function of time is presented as two images: the left image is the signal in the red channel and the right image is that detected in the green channel. The alleles appear at 17 minutes after injection. The signal in the red channel is predominantly from the red-labeled standard ladder and the expected 4 band patterns are seen in all capillaries. The unknown, amplified with the green emitting primer, is detected in the green channel. Allelic bands are identified as the intense green bands coinciding in mobility with allelic ladder bands in the red channel. To illustrate, the right image of FIG. 18 reveals intense green bands corresponding to allele 7 in lane 1, alleles 9+9.3 in lane 2, alleles 6+9.3 in lane 3, alleles 7+8 in lane 4, and allele 9 in lane 5. FIG. presents electropherograms derived from the image in FIG. 18. Very clear discrimination is observed between the green-labeled fragments and the red-labeled fragments with almost no cross-talk between the green and red channels. In some cases, the amplification products of heterozygote samples contain heteroduplex bands that migrate behind the allelic ladder. Additional weak "noise" bands may represent non-templated base addition (Kimpton et al. (1993) PCR Methods and Applications 3, 13–22) known to occur with PCR amplification of THO1.

The accuracy and precision of allelic sizing using CAE was tested by performing multiple runs on 11 different samples. These results are summarized in Table 1.

TABLE 1

| Statistical analysis of THO1 fragment sizing[1] | | | | |
|---|---|---|---|---|
| Allele | Length (bp) | Determinations | Mean size[2] | S.D. (%)[3] |
| 6 | 183 | 6 | 183.1 | 0.61 (0.33) |
| 7 | 187 | 23 | 187.0 | 0.41 (0.22) |
| 8 | 191 | 15 | 191.2 | 0.69 (0.36) |
| 9 | 195 | 11 | 195.4 | 0.60 (0.31) |
| 9.3 | 198 | 8 | 198.3 | 0.52 (0.26) |
| 10 | 199 | 6 | 199.0 | 0.31 (0.15) |

[1]Eleven different amplified samples (7, 8), (6, 9.3), (9, 9.3), (6, 9), (7, 8), (8, 9), (7, 9.3), (7, 10), 6, 9.3), (7) and (9) were run 8, 2, 4, 3, 5, 2, 1, 6, 1, 3 and 2 times, respectively.
[2]Mean PCR product size as determined by linear regression using the allelic ladder as the sizing standard.
[3]Standard Deviation in terms of base pairs for the indicated number of determinations. The percent relative S.D. is given in parentheses.

Since a linear relationship exists between molecular weight and migration time in the region of interest, the allelic ladder was used with a linear regression analysis to size the unknown fragments. The calculated sizes of unknown alleles are compared to true sizes based on sequence analysis and verified by denaturing polyacrylamide gel electrophoresis. The average absolute difference of the determined allele sizes from the true allele sizes was 0.41 and over 70% of the determined values were within 0.5 bp of the true value. The reproducibility is excellent (relative standard deviation less than 0.4% for each allele) and there was no ambiguity in allele assignments. Two alleles, 9.3 and 10, which differ by a single base pair deletion can not be electrophoretically resolved when paired but can be correctly assigned when in combination with any other allele. It should however be possible to separate these two fragments or columns containing higher concentrations of HEC.

8. Two-Color Sizing of Multiplexed STRs.

Figure 20A:
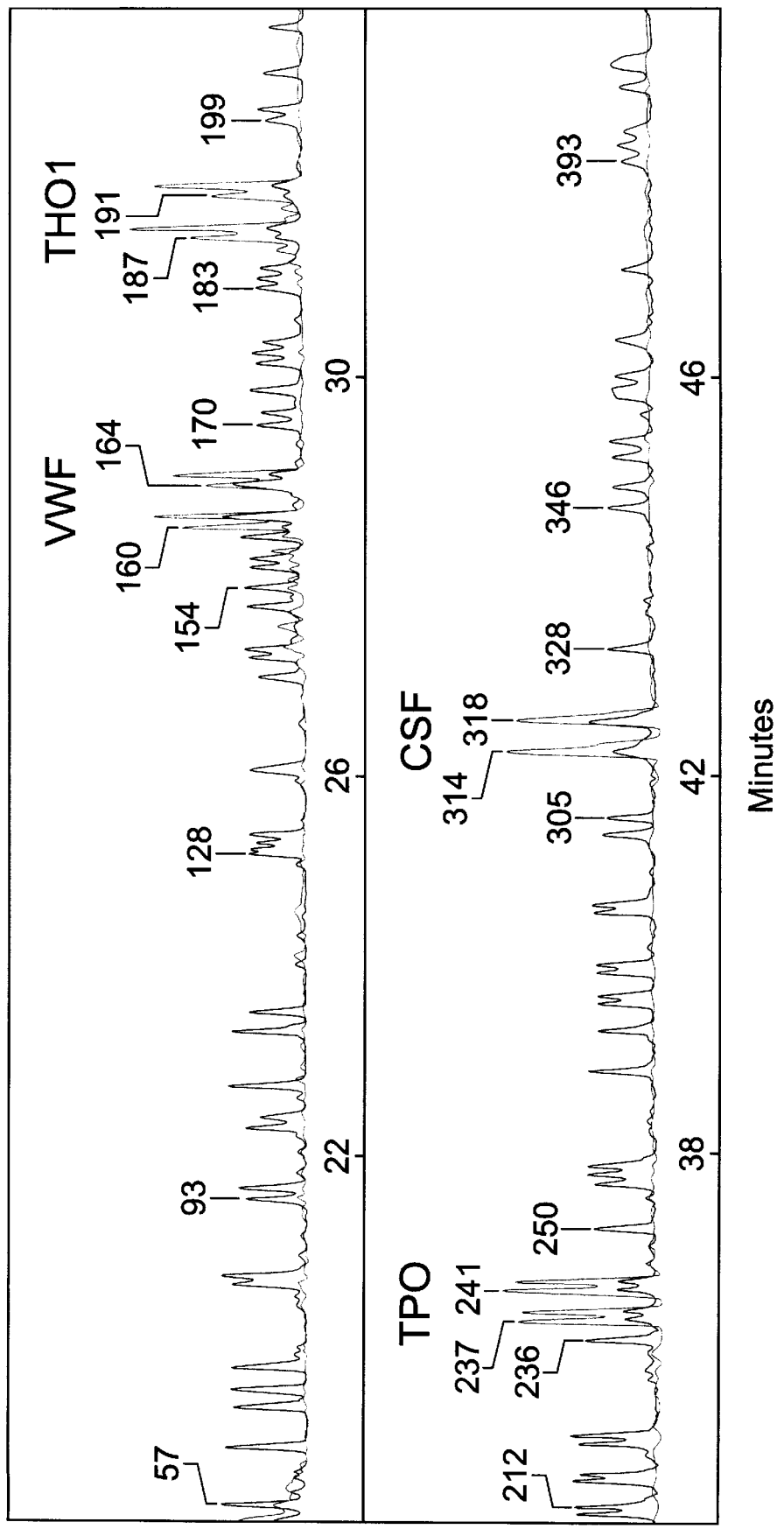
FIG. 20 shows representative electropherograms of three different multiplexed STR samples typed for VWFA, THO1, TPO and CSF loci (green). Each set of fragments is sized against an M13 A-termination standard generated with the F10R primer. Electrophoresis was performed with replaceable 2% HEC, 1×TBE, 6 M urea, 10% formamide sieving matrices at 200 V/cm. This figure has been processed with matrix transformation to correct for the spectral cross-talk between channels.
Figure 21:
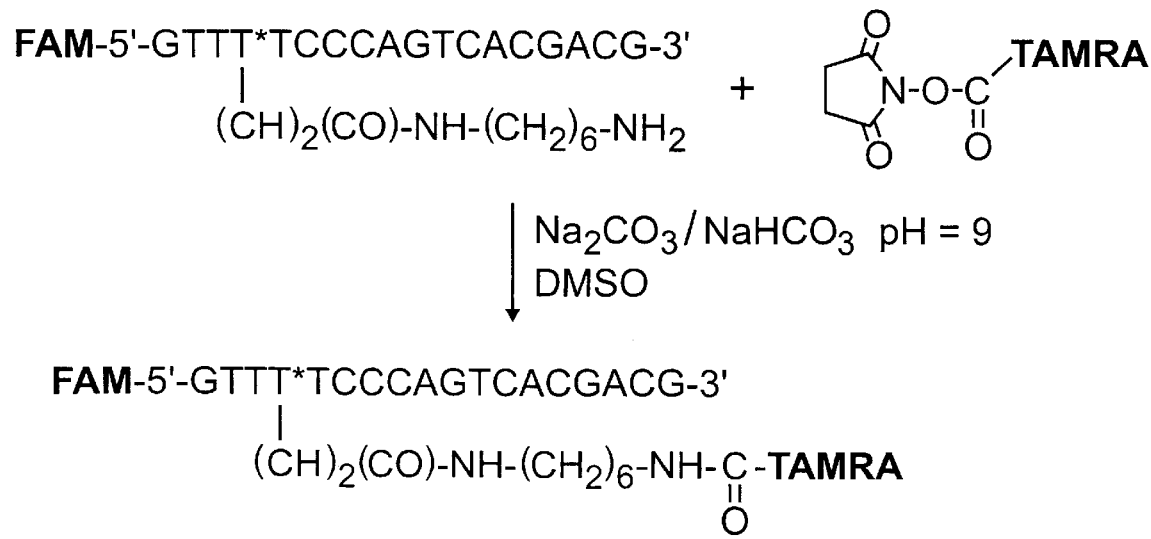
FIG. 21. Structures of twenty energy transfer (ET) primers (SEQ ID NOs:2–21) and a representative synthetic scheme for the preparation of F3T (SEQ ID NOs:22 and 12).
Figure 22:
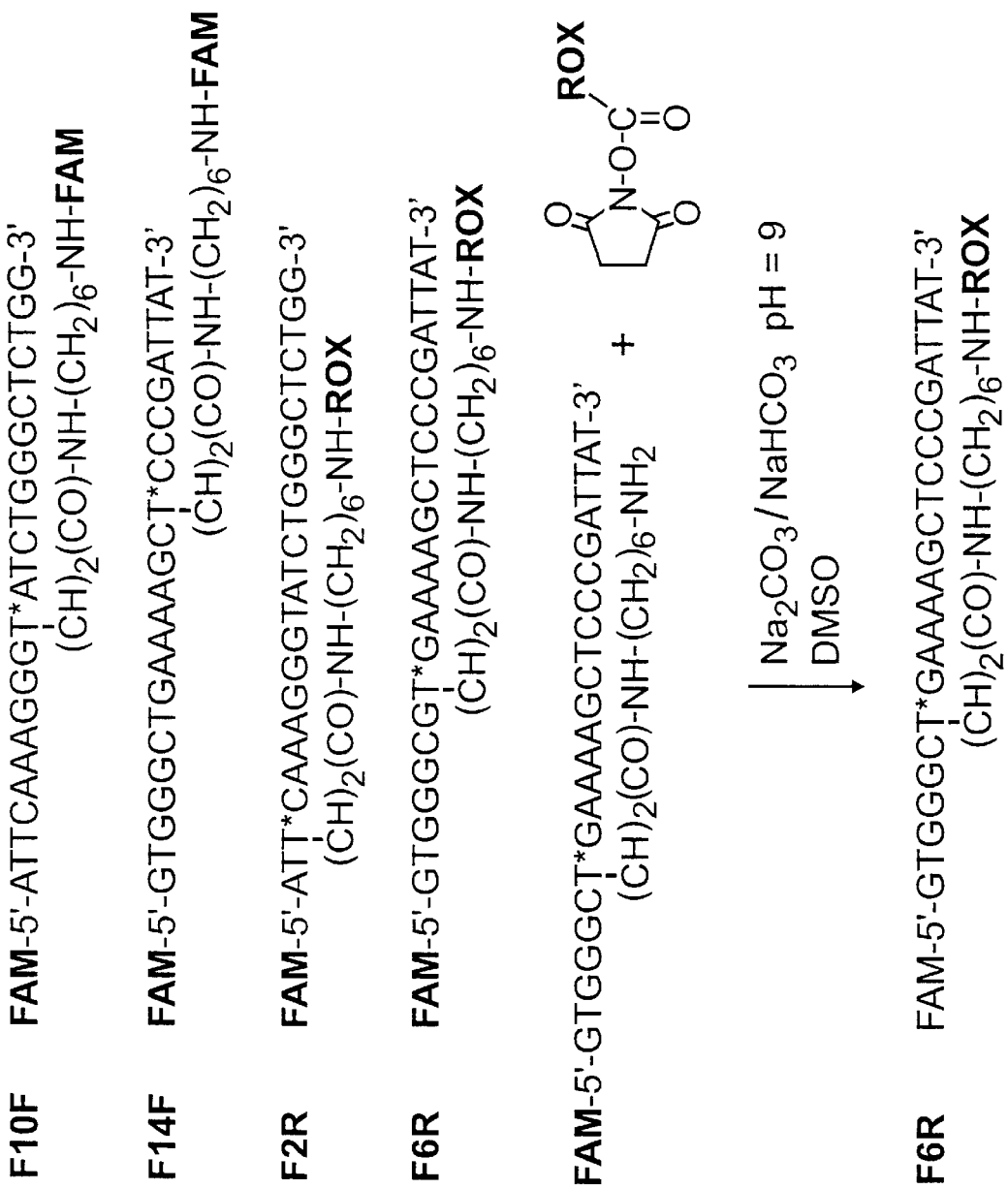
FIG. 22. Structures of the four energy transfer (ET) primers (SEQ ID NOs:23–26) and a representative synthetic scheme for the preparation of F6R (SEQ ID NOs:27 and 26). The fluorescent primers are labeled with a common fluorescein donor (F) at the 5' end and either a second fluorescein or a rhodamine (R) acceptor at the indicated locations of a modified T in the sequence. The number of nucleotides between the two fluorophores is indicated in the primer designation.

FIG. 20 presents three different capillary array electrophoresis separations of the VWFA, THO1, TPO and CSF STR tetraplex. Denaturing and replaceable HEC separation sieving matrices were used to achieve rapid (<50 min) separations. The VWFA, TPO and CSF loci were amplified with an F8F primer and the THO1 locus was amplified with an F6F primer. The data in FIG. 20 demonstrate that the four loci are evenly amplified. Since they are amplified with the F8F or F6F primers, they are only detected in the green channel. The cross-talk in the red M13 channel is low and can be easily removed by appropriate software filtering. Each locus is heterozygous except the CSF locus in trace C.

In these runs, each allele is represented by doublet peaks; the first peak of each doublet is the desired PCR product and the second peak is a non-templated one-base addition.

In this study, we have investigated the use of an M13 sequencing ladder as a universal fragment sizing calibration standard; this standard is easily prepared from commercially available M13 templates. M13 A-, T-, C- and G-track ladders were individually prepared and tested singly and in paired combinations. The single track and pair track ladders were evaluated for evenness of peak distribution over the sizing range of interest (100–350 nucleotides), position of the landmark peaks to put the ladder into register, and linearity of the correlation of size to mobility. The M13 A-track was found to provide the best combination of peak spacing and linear correlation of size to mobility. Some compressions appeared in the C and G track ladders although the deviation from a linear correlation was small. The T-track had large gaps over the size range of interest. The M13 A-track was produced using an F10R labeled sequencing primer and was detected in the red channel.

Single base resolution is routinely achieved for the separation of M13 A-fragments up to 400 bp. The importance of single base resolution is illustrated in Trace C of FIG. 20 which shows the separation of the 9.3 and 10 alleles at the THO1 locus. Alleles 9.3 and 10, which differ by a single base deletion, produce a triplet peak in the electropherogram. The first peak is the desired 9.3 PCR product. The middle peak with high intensity is the overlap of the one-base addition to allele 10. For the THO1 locus the triplet structure is a nice indicator of the appearance of alleles 9.3 and 10. Lengthening the time of the final PCR extension reaction to 2 h or more results in near complete production of the non-templated base addition product, thus by-passing any interpretive ambiguity associated with this phenomenon. The extra peak in the high molecular weight allele of the TPO locus in Trace C is much stronger than the expected doublet peaks and this could be due to false PCR amplification.

It is evident from the above results, that one can tune related compositions, e.g. polynucleotides functionalized with 2 fluorophores to provide for different emission wavelengths and high emission quantum yields, while having substantially the same excitation-light absorbance and mobility. The subject labels can be readily prepared, can be used in a wide variety of contexts, and have good stability and enhanced fluorescent properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fluorescent label comprising:

at least two fluorophores bonded to a polymeric backbone at specific locations thereon to form a chemically pure label wherein at least one fluorophore is bonded to a terminal monomeric unit of said polymeric backbone and the other fluorophore(s) is bonded to a non-terminal monomeric unit of said polymeric backbone and said terminally bonded fluorophore is in an energy transfer relationship with said other fluorophore(s), said fluorophores comprising a donor fluorophore and an acceptor fluorophore of which said donor fluorophore absorbs light in the wavelength range of 350 to 800 nm and said acceptor emits light in the wavelength range of 450 to 1000 nm.

2. The label according to claim 1, wherein the difference between the emission maxima of said donor and acceptor fluorophores does not exceed 100 nm.

3. The label according to claim 1, wherein the distance in monomeric units of said polymer between said donor and acceptor fluorophores ranges from about 2 to 20.

4. The label according to claim 1, wherein the monomeric units of said polymer comprise bases selected from the group consisting of purines, pyrimidines and hybridizing analogues thereof.

5. The label according to claim 4, wherein said polymer is an oligonucleotide.

6. The label according to claim 4, wherein said polymer is a peptide nucleic acid.

7. The label according to claim 5, wherein said donor fluorophore is bonded to the 5' terminus of said olgonucleotide.

8. The label according to claim 5, wherein said acceptor donor fluorophore is bonded to the 5' terminus of said oligonucleotide.

9. A fluorescent label comprising:

at least two fluorophores comprising a donor fluorophore and an acceptor fluorophore bonded to an oligonucleotide at specific locations thereon to form a chemically pure label, wherein one of said fluorophores is bonded to the 5' terminus of said oligonucleotide and the other of said fluorophores is bonded to a modified nucleotide from 2 to 20 nucleotides 3' of said 5' bonded fluorophore and said 5' bonded fluorophore is in energy transfer relationship with said other fluorophore, and wherein said donor fluorophore absorbs light in the wavelength range of 350 to 800 nm and said acceptor fluorophore emits light in the wavelength range of 450 to 1000 nm.

10. The label according to claim 9, wherein said oligonucleotide is from 3 to 30 nucleotides.

11. The label according to claim 9, wherein said donor and acceptor flurorophores are bonded to said oligonucleotide through a linker arm.

12. The label according to claim 9, wherein the difference between the emission maxima of said donor and acceptor fluorophores does not exceed 100 nm.

13. The label according to claim 9, wherein said 5' bonded fluorophore is bonded to the phosphate group of the 5' nucleotide.

14. The label according to claim 9, wherein said 5' bonded fluorophore is bonded to the sugar group of the 5' nucleotide.

15. The label according to claim 9, wherein said 5' bonded fluorophore is bonded to a modified base of the 5' nucleotide.

16. A fluorescent label comprising:

donor and acceptor fluorophores having a difference in emission maxima that does not exceed 100 nm bonded to an oligonucleotide at specific locations thereon to form a chemically pure label, wherein one of said donor and acceptor fluorophores is bonded to the 5' terminus of said oligonucleotide and the other of said donor and acceptor fluorophores is bonded to a modified nucleotide from 2 to 20 nucleotides 3' of said 5' bonded fluorophore.

17. The label according to claim 16, wherein at least one of said donor and acceptor fluorophores is a xanthene compound.

18. The label according to claim 16, wherein said xanthene compound is fluorescein or rhodamine.

19. The label according to claim 16, wherein said 5' bonded fluorophore is bonded to the sugar group of the 5' nucleotide of said oligonucleotide.

20. The label according to claim 16, wherein said 5' bonded fluorophore is bonded to a modified base of the 5' nucleotide.

21. The label according to claim 16, wherein said modified nucleotide is Amino Modifier C6 dT.

22. A fluorescent label comprising:

a donor fluorophore and an acceptor fluorophore having a difference in emission maxima that does not exceed 100 nm bonded to an oligonucleotide at specific locations thereon to form a chemically pure label, wherein one of said donor and acceptor fluorophores is bonded to the sugar group of the 5' nucleotide of said oligonucleotide and the other of said donor and acceptor fluorophores is bonded to a modified nucleotide from 2 to 15 nucleotides 3' of 5' bonded fluorophore, wherein said modified nucleotide is Amino Modifier C6 dT.

23. The label according to claim 22, wherein said donor is FAM and said acceptor is selected from the group consisting of JOE, TAMRA, ROX, 6-carboxyrhodamine-6G and 5-carboxyrhodamine-6G.

24. A fluorescent label having a donor fluorophore and an acceptor fluorophore bonded to an oligonucleotide at specific locations thereon to form a chemically pure label, wherein said donor fluorophore is bonded to the sugar group of the 5' nucleotide of said oligonucleotide and said acceptor fluorophore is bonded to a modified nucleotide 3' of said 5' bonded fluorophore, said label described by the formula:

$$D-N-A$$

wherein:

D is FAM;

N is the number of bases between said donor fluorophore and said acceptor fluorophore and ranges from 2 to 14; and A is FAM.

25. A fluorescent label having a donor fluorophore and an acceptor fluorophore bonded to an oligonucleotide at specific locations thereon to form a chemically pure label, wherein said donor fluorophore is bonded to the sugar group of the 5' nucleotide of said oligonucleotide and said acceptor fluorophore is bonded to a modified nucleotide 3' of said 5' bonded fluorophore, said label described by the formula:

$$D-N-A$$

wherein:

D is FAM;

N is the number of bases between said donor fluorophore and said acceptor fluorophore and ranges from 2 to 14; and A is JOE.

26. A fluorescent label having a donor fluorophore and an acceptor fluorophore bonded to an oligonucleotide at specific locations thereon to form a chemically pure label, wherein said donor fluorophore is bonded to the sugar group of the 5' nucleotide of said oligonucleotide and acceptor fluorophore is bonded to a modified nucleotide 3' of said 5' bonded fluorophore, said label described by the formula:

$$D-N-A$$

wherein:

D is FAM;

N is the number of bases between said donor fluorophore and said acceptor fluorophore and ranges from 2 to 14; and A is TAMRA.

27. A fluorescent label having a donor fluorophore and an acceptor fluorophore bonded to an oligonucleotide at specific locations thereon to form a chemically pure label, wherein said donor fluorophore is bonded to the sugar group of the 5' nucleotide of said oligonucleotide and said acceptor fluorophore is bonded to a modified nucleotide 3' of said 5' bonded fluorophore, said label described by the formula:

$$D-N-A$$

wherein:

D is FAM;

N is the number of bases between said donor fluorophore and said acceptor fluorophore and ranges from 2 to 14; and A is ROX.

* * * * *